United States Patent
Boy et al.

(10) Patent No.: US 6,933,308 B2
(45) Date of Patent: Aug. 23, 2005

(54) AMINOALKYL THIAZOLE DERIVATIVES AS KCNQ MODULATORS

(75) Inventors: Kenneth M. Boy, Durham, CT (US); Yong-Jin Wu, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 28 days.

(21) Appl. No.: 10/730,781

(22) Filed: Dec. 9, 2003

(65) Prior Publication Data

US 2004/0138268 A1 Jul. 15, 2004

Related U.S. Application Data

(60) Provisional application No. 60/435,971, filed on Dec. 20, 2002.

(51) Int. Cl.$^7$ .................. C07D 277/20; C07D 295/02; C07D 213/02; A61K 31/427; A61P 25/08
(52) U.S. Cl. ............... 514/365; 548/200; 544/111; 546/269.7; 514/231.5; 514/342
(58) Field of Search ............ 548/200; 544/111; 546/269.7; 514/365, 231.5, 342

(56) References Cited

U.S. PATENT DOCUMENTS

| | | |
|---|---|---|
| 3,689,481 A | 9/1972 | Scheuermann et al. |
| 3,794,636 A | 2/1974 | Girgis |
| 3,872,124 A | 3/1975 | LeMartret et al. |
| 4,923,886 A | 5/1990 | Shiokawa et al. |
| 4,980,363 A | 12/1990 | Shimotori et al. |
| 5,045,554 A | 9/1991 | Alt et al. |
| 5,057,142 A | 10/1991 | Baasner et al. |
| 5,244,867 A | 9/1993 | Ditrich et al. |
| 5,330,995 A | 7/1994 | Eicken et al. |
| 5,614,520 A | 3/1997 | Kondo et al. |
| 5,846,990 A | 12/1998 | Murugesan et al. |
| 5,859,035 A | 1/1999 | Anthony et al. |
| 5,888,941 A | 3/1999 | Bartroli et al. |
| 6,319,940 B1 | 11/2001 | Elbe et al. |

FOREIGN PATENT DOCUMENTS

| | | |
|---|---|---|
| JP | 57183768 | 11/1982 |
| JP | 01250379 | 10/1989 |
| JP | 02229190 | 9/1990 |
| JP | 04049290 | 2/1992 |
| JP | 04128275 | 4/1992 |
| WO | WO 95/19972 | 7/1995 |
| WO | WO 98/28282 | 7/1998 |
| WO | WO 99/59570 | 11/1999 |
| WO | WO 99/66925 | 12/1999 |
| WO | WO 00/06085 | 2/2000 |
| WO | WO 01/10798 | 2/2001 |
| WO | WO 01/40207 A1 | 6/2001 |

OTHER PUBLICATIONS

Robbins Pharmacology & Therapeutics 90: 1–19, 2001.*
Jensen, CNS Drug Rev. 8(4): 353–60, 2002.*
H.–S. Wang, et al, "KCNQ2 and KCNQ3 Potassium Channel Subunits: Molecular Correlates of the M–Channel," SCIENCE, 282, pp. 1890–1893, 1998.

* cited by examiner

*Primary Examiner*—Venkataraman Balasubramanian
(74) *Attorney, Agent, or Firm*—James Epperson

(57) ABSTRACT

Novel aminoalkylthiazole derivatives of Formula I are described which are openers of KCNQ potassium channels and are useful in the treatment of disorders responsive to the opening of the KCNQ potassium channels, including pain and migraine.

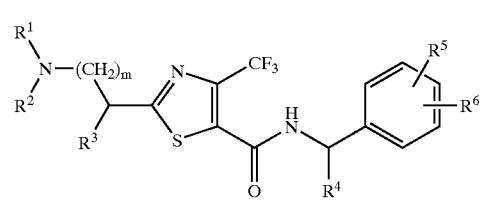

11 Claims, No Drawings

AMINOALKYL THIAZOLE DERIVATIVES AS KCNQ MODULATORS

REFERENCE TO RELATED APPLICATIONS

This application claims the benefit of U.S. provisional application No. 60/435,971, filed Dec. 20, 2002.

BACKGROUND OF THE INVENTION

The present invention is directed to novel aminoalkylthiazole compounds which are modulators of KCNQ potassium channels and are useful in treating disorders responsive to the modulation of the potassium channels. The invention also provides pharmaceutical compositions and methods of treatment with the novel aminoalkylthiazol compounds.

Potassium ($K^+$) channels are a diverse class of ion channels and have several critical roles in cell function. One role is in neurons, where $K^+$ channels are responsible, in part, for determining cell excitability by contributing to membrane repolarization following depolarization, resting membrane potential, and regulation of neurotransmitter release. The M-current, measured by electrophysiology recording methods and by pharmacology, has been described as a dominant conductance in controlling neuronal excitability. Pharmacological activation or suppression of M-currents by small molecules could have profound effects in controlling neuronal excitability. Recently, Wang reported that co-assembly of the KCNQ2 and KCNQ3 potassium channels underlies the native M-current in neurons (Wang et al., *Science* 1998, 282, 1890–1893).

Activation or opening of the KCNQ channels, particularly the KCNQ2 or KCNQ2/3 channels, mutated or wild type, may be beneficial for increasing hyperpolarization of neurons, thereby resulting in protection from abnormal synchronous firing during a migraine attack. This invention provides a solution to the problem of abnormal synchronous firing of neurons related to migraine headache by demonstrating that modulators, preferably openers, of KCNQ potassium channels increase hyperpolarization of neurons. This leads to protection against abnormal synchronous neuron firing involved in migraine attacks.

Although the symptom pattern varies among migraine sufferers, the severity of migraine pain justifies a need for vigorous, yet safe and effective, treatments and therapies for the great majority of cases. A need exists for agents that can be used to combat and relieve migraine (and diseases similar to and mechanistically related to migraine), as well as prevent the recurrence of migraine. Also needed are abortive anti-migraine agents, effective in the treatment of acute migraine, as well as in the prodrome phase of a migraine attack. Thus, a clear goal in the art is to discover new, safe, nontoxic and effective anti-migraine compounds and their pharmaceutical compositions for use in anti-migraine treatments.

Because migraine afflicts a large percentage of the population, there is a need to discover compounds and agents that are useful in therapeutics and treatments, and as components of pharmaceutical compositions, for treating the pain and discomfort of migraine headache and other symptoms of migraine. This invention satisfies this need by providing compounds that function as openers of the KCNQ family of potassium ion channels and act as anti-migraine agents.

A number of thiazole derivatives have been disclosed. These references do not teach or suggest the compounds of this invention. See the following: WO 01/40207 A1, JP 04128275 A2, U.S. Pat. No. 5,244,867, U.S. Pat. No. 4,980,363, U.S. Pat. No. 5,846,990, JP 04049290 A2, WO 99/66925 A1, U.S. Pat. No. 5,888,941, U.S. Pat. No. 3,794,636, JP 57183768 A2, U.S. Pat. No. 5,057,142, U.S. Pat. No. 5,859,035, JP 02229190 A2, WO 98/28282 A2, WO 00/06085 A2, U.S. Pat. No. 5,614,520, U.S. Pat. No. 3,689,481, JP 01250379 A2, U.S. Pat. No. 3,872,124, U.S. Pat. No. 4,923886, WO 99/59570 A1, WO 01/10798 A1, and WO 95/19972 A1.

SUMMARY OF THE INVENTION

The invention encompasses novel aminoalkylthiazole compounds and related derivatives of Formula I.

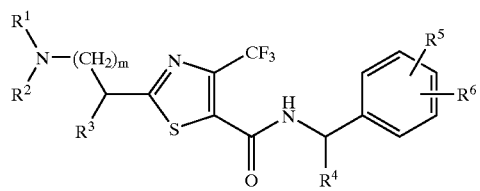

The compounds are openers or activators of KCNQ potassium channels. The invention also describes pharmaceutical compositions methods of treatment of disorders sensitive to KCNQ potassium channel opening activity.

DETAILED DESCRIPTION OF THE INVENTION

The invention encompasses compounds of Formula I and related derivatives, including pharmaceutically acceptable salts and solvates,

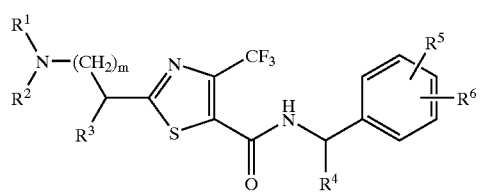

where:
$R^1$ is $C_{1-6}$alkyl, $C_{3-7}$cycloalkyl, —$(CH_2)_{1-4}C_{3-7}$cycloalkyl, —$(CH_2)_{2-4}N(C_{1-6}alkyl)_2$, —$(CH_2)_{2-4}OC_{1-6}$alkyl,

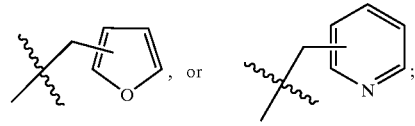

$R^2$ is hydrogen, $C^{1-6}$alkyl, or —$(CH_2)_{2-4}OC_{1-6}$alkyl;
or where $R^1$ and $R^2$ taken together are —$CH_2CH_2XCH_2CH_2$—, where X is a chemical bond, $CH_2$, CHOH, NH, $NCH_3$, $NCOCH_3$, O, or S;
$R^3$ is hydrogen or hydroxy, provided that where $R^3$ is hydroxy, m is not 0;
$R^4$ is hydrogen, $C_{1-6}$alkyl, —$CH_2OH$, or trifluoromethyl;
$R^5$ is halogen, $C_{1-6}$alkyl, $C_{1-2}$perfluoroalkyl, $C_{1-6}$alkoxy, $C_{1-2}$perfluoroalkoxy, —$N(R^4)_2$, N-morpholinyl, or pyridyl;
$R^6$ is hydrogen, halogen, or $C_{1-6}$alkoxy;
m is 0 or 1.

"$C_{1-6}$ alkyl" means straight or branched chain alkyl groups such as methyl, ethyl, propyl, isopropyl, butyl, isobutyl, and tert-butyl. "$C_{1-6}$ alkoxy" means an oxygen substituted with straight or branched chain alkyl groups and includes groups such as methoxy, ethoxy, propoxy, isopropoxy, butoxy, isobutoxy, and tert-butoxy.

"KCNQ" means the family of polypeptides that have been described as KCNQ2, KCNQ3, KCNQ4, and KCNQ5 potassium channels as well as heteromultimers of different members. For example, KCNQ2/3, KCNQ2/5 and KCNQ3/5.

The term "pain" includes all types of acute and chronic pain, such as migraine or a migraine attack, cluster headaches, musculoskeletal pain, post-operative pain, surgical pain, inflammatory pain, neuropathic pain such as diabetic neuropathy and pain associated with cancer and fibromyalgias, chronic lower back pain, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis. The term is also intended to include nociceptive pain or nociception.

"Therapeutically effective amount" means the amount of a compound required to elicit a meaningful patient benefit. For example, the amount of compound or composition necessary to improve a clinical parameter or ameliorate a symptom.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention also includes all solvated forms of the instant compounds, particularly hydrates. Solvates do not contribute significantly to the physiological activity or toxicity of the compounds and as such function as pharmacological equivalents. Solvates may form in stoichiometric amounts or may form from adventitious solvent or a combination of both. One type of solvate is hydrate, and some hydrated forms include monohydrate, hemihydrate, and dihydrate.

Some of the compounds of the invention possess asymmetric carbon atoms, such as the carbon atom bearing $R^1$ in Formula Id. The invention includes all stereoisomeric forms. Stereoisomeric mixtures of the compounds and related intermediates can be separated into individual isomers according to methods commonly known in the art.

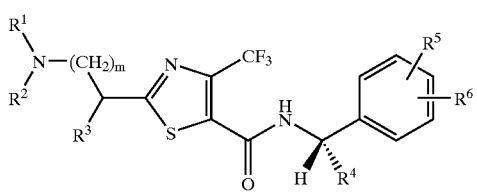

Id

One aspect of the present invention are compounds of Formula I where m is 1.

Another aspect of the invention are compounds of Formula I where $R^3$ is hydrogen.

Another aspect of the invention are compounds of Formula I where $R^3$ is hydroxy and m is 1.

Another aspect of the invention are compounds of Formula I where $R^4$ is methyl.

Another aspect of the invention are compounds of Formula I where the structure is that of Formula Ie.

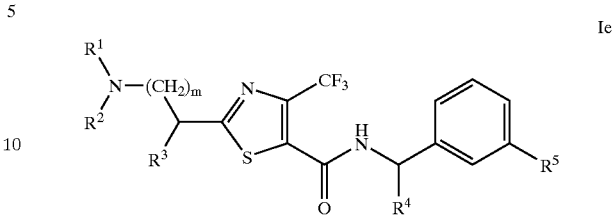

Ie

Another aspect of the invention are compounds of Formula I where the structure has the stereochemical configuration of Formula Id.

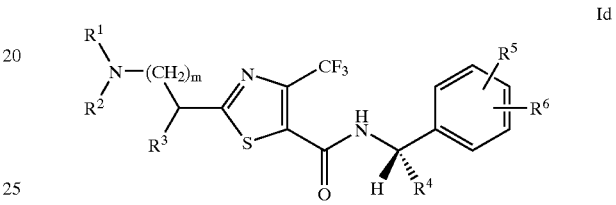

Id

Some compounds of the invention include the following:

(1) 2-[2-(4-morpholinyl)ethyl]-N-[1-[3-(3-pyridinyl)phenyl]ethyl]-4-(trifluoromethyl)-5-thiazolecarboxamide;

(2) N-[1-[3-(dimethylamino)phenyl]ethyl]-2-[2-(1-pyrrolidinyl)ethyl]-4-(trifluoromethyl)-5-thiazolecarboxamide;

(3) 2-[2-(1-pyrrolidinyl)ethyl]-4-(trifluoromethyl)-N-[1-[3-(trifluoromethyl)phenyl]ethyl]-5-thiazolecarboxamide;

(4) 2-[2-[(2-furanylmethyl)methylamino]ethyl]-N-[(1S)-1-[3-(4-morpholinyl)phenyl]ethyl]-4-(trifluoromethyl)-5-thiazolecarboxamide;

(5) 2-[2-[(2-furanylmethyl)methylamino]ethyl]-N-[1-[3-(3-pyridinyl)phenyl]ethyl]-4-(trifluoromethyl)-5-thiazolecarboxamide;

(6) 2-[2-(1-pyrrolidinyl)ethyl]-N-[1-[3-(trifluoromethoxy)phenyl]ethyl]-4-(trifluoromethyl)-5-thiazolecarboxamide;

(7) 2-[2-[(2-furanylmethyl)methylamino]ethyl]-N-[1-[3-(trifluoromethoxy)phenyl]ethyl]-4-(trifluoromethyl)-5-thiazolecarboxamide;

(8) 2-[2-(diethylamino)ethyl]-N-[1-[3-(trifluoromethoxy)phenyl]ethyl]-4-(trifluoromethyl)-5-thiazolecarboxamide;

(9) 2-[2-(diethylamino)ethyl]-N-[1-[3-(dimethylamino)phenyl]ethyl]-4-(trifluoromethyl)-5-thiazolecarboxamide;

(10) 2-[2-[ethyl(4-pyridinylmethyl)amino]ethyl]-4-(trifluoromethyl)-N-[1-[3-(trifluoromethyl)phenyl]ethyl]-5-thiazolecarboxamide;

(11) 2-[2-(4-thiomorpholinyl)ethyl]-4-(trifluoromethyl)-N-[1-[3-(trifluoromethyl)phenyl]ethyl]-5-thiazolecarboxamide;

(12) 2-[2-[[2-(dimethylamino)ethyl]methylamino]ethyl]-N-[1-[3-(trifluoromethoxy)phenyl]ethyl]-4-(trifluoromethyl)-5-thiazolecarboxamide;

(13) 2-[2-[[2-(dimethylamino)ethyl]methylamino]ethyl]-4-(trifluoromethyl)-N-[1-[3-(trifluoromethyl)phenyl]ethyl]-5-thiazolecarboxamide;

(14) 2-[2-(4-methyl-1-piperazinyl)ethyl]-N-[1-[3-(trifluoromethoxy)phenyl]ethyl]-4-(trifluoromethyl)-5-thiazolecarboxamide;

(15) 2-[2-(1-piperidinyl)ethyl]-N-[1-[3-(trifluoromethoxy)phenyl]ethyl]-4-(trifluoromethyl)-5-thiazolecarboxamide;
(16) N-[1-[3-(dimethylamino)phenyl]ethyl]-2-[2-(1-piperidinyl)ethyl]-4-(trifluoromethyl)-5-thiazolecarboxamide;
(17) 2-[2-(1-piperidinyl)ethyl]-4-(trifluoromethyl)-N-[1-[3-(trifluoromethyl)phenyl]ethyl]-5-thiazolecarboxamide;
(18) N-[(1S)-1-[3-(4-morpholinyl)phenyl]ethyl]-2-[2-(1-piperidinyl)ethyl]-4-(trifluoromethyl)-5-thiazolecarboxamide;
(19) 2-[2-(4-hydroxy-1-piperidinyl)ethyl]-N-[1-[3-(trifluoromethoxy)phenyl]ethyl]-4-(trifluoromethyl)-5-thiazolecarboxamide;
(20) 2-[2-(4-hydroxy-1-piperidinyl)ethyl]-4-(trifluoromethyl)-N-[1-[3-(trifluoromethyl)phenyl]ethyl]-5-thiazolecarboxamide;
(21) 2-[2-[(cyclopropylmethyl)propylamino]ethyl]-N-[1-[3-(trifluoromethoxy)phenyl]ethyl]-4-(trifluoromethyl)-5-thiazolecarboxamide;
(22) 2-[2-[(cyclopropylmethyl)propylamino]ethyl]-N-[1-[3-(dimethylamino)phenyl]ethyl]-4-(trifluoromethyl)-5-thiazolecarboxamide;
(23) 2-[2-[(cyclopropylmethyl)propylamino]ethyl]-4-(trifluoromethyl)-N-[1-[3-(trifluoromethyl)phenyl]ethyl]-5-thiazolecarboxamide;
(24) 2-[2-(diethylamino)ethyl]-N-[(1S)-1-[3-(3-pyridinyl)phenyl]ethyl]-4-(trifluoromethyl)-5-thiazolecarboxamide;
(25) 2-[2-(1-piperidinyl)ethyl]-N-[(1S)-1-[3-(3-pyridinyl)phenyl]ethyl]-4-(trifluoromethyl)-5-thiazolecarboxamide;
(26) 2-[2-[(1-ethylpropyl)amino]ethyl]-N-[1-[3-(trifluoromethoxy)phenyl]ethyl]-4-(trifluoromethyl)-5-thiazolecarboxamide;
(27) 2-[2-[(1-ethylpropyl)amino]ethyl]-4-(trifluoromethyl)-N-[1-[3-(trifluoromethyl)phenyl]ethyl]-5-thiazolecarboxamide;
(28) 2-[2-[(2-furanylmethyl)amino]ethyl]-N-[(1S)-1-[3-(3-pyridinyl)phenyl]ethyl]-4-(trifluoromethyl)-5-thiazolecarboxamide;
(29) 2-[2-(cyclopentylamino)ethyl]-N-[1-[3-(trifluoromethoxy)phenyl]ethyl]-4-(trifluoromethyl)-5-thiazolecarboxamide;
(30) 2-[2-(cyclopentylamino)ethyl]-N-[(1S)-1-[3-(3-pyridinyl)phenyl]ethyl]-4-(trifluoromethyl)-5-thiazolecarboxamide;
(31) 2-[2-[bis(2-methoxyethyl)amino]ethyl]-N-[1-[3-(trifluoromethoxy)phenyl]ethyl]-4-(trifluoromethyl)-5-thiazolecarboxamide;
(32) 2-[2-[bis(2-methoxyethyl)amino]ethyl]-4-(trifluoromethyl)-N-[1-[3-(trifluoromethyl)phenyl]ethyl]-5-thiazolecarboxamide;
(33) 2-[2-[bis(2-methoxyethyl)amino]ethyl]-N-[(1S)-1-[3-(3-pyridinyl)phenyl]ethyl]-4-(trifluoromethyl)-5-thiazolecarboxamide;
(34) 2-[2-(4-morpholinyl)ethyl]-N-[(1S)-1-[3-(4-morpholinyl)phenyl]ethyl]-4-(trifluoromethyl)-5-thiazolecarboxamide;
(35) N-[1-[3-(dimethylamino)phenyl]ethyl]-2-[2-(4-thiomorpholinyl)ethyl]-4-(trifluoromethyl)-5-thiazolecarboxamide;
(36) 2-[2-[[2-(dimethylamino)ethyl]methylamino]ethyl]-N-[1-[3-(dimethylamino)phenyl]ethyl]-4-(trifluoromethyl)-5-thiazolecarboxamide;
(37) 2-[2-(4-methyl-1-piperazinyl)ethyl]-N-[(1S)-1-[3-(4-morpholinyl)phenyl]ethyl]-4-(trifluoromethyl)-5-thiazolecarboxamide;
(38) 2-[2-(diethylamino)ethyl]-N-[1-[3-(trifluoromethoxy)phenyl]ethyl]-4-(trifluoromethyl)-5-thiazolecarboxamide;
(39) 2-[2-(4-thiomorpholinyl)ethyl]-4-(trifluoromethyl)-N-[1-[3-(trifluoromethyl)phenyl]ethyl]-5-thiazolecarboxamide;
(40) 2-[1-hydroxy-2-(1-piperidinyl)ethyl]-N-[1-[3-(trifluoromethoxy)phenyl]ethyl]-4-(trifluoromethyl)-5-thiazolecarboxamide;
(41) 2-[1-hydroxy-2-(1-pyrrolidinyl)ethyl]-4-(trifluoromethyl)-N-[1-[3-(trifluoromethyl)phenyl]ethyl]-5-thiazolecarboxamide;
(42) 2-[2-[(2-furanylmethyl)methylamino]-1-hydroxyethyl]-4-(trifluoromethyl)-N-[1-[3-(trifluoromethyl)phenyl]ethyl]-5-thiazolecarboxamide;
(43) 2-[2-[(cyclopropylmethyl)propylamino]-1-hydroxyethyl]-N-[1-[3-(trifluoromethoxy)phenyl]ethyl]-4-(trifluoromethyl)-5-thiazolecarboxamide;
(44) 2-[2-(diethylamino)-1-hydroxyethyl]-N-[(1S)-1-[3-(4-morpholinyl)phenyl]ethyl]-4-(trifluoromethyl)-5-thiazolecarboxamide;
(45) 2-[2-(diethylamino)-1-hydroxyethyl]-N-[(1S)-1-[3-(3-pyridinyl)phenyl]ethyl]-4-(trifluoromethyl)-5-thiazolecarboxamide;
(46) 2-[1-hydroxy-2-(4-morpholinyl)ethyl]-N-[1-[3-(trifluoromethoxy)phenyl]ethyl]-4-(trifluoromethyl)-5-thiazolecarboxamide;
(47) 2-[1-hydroxy-2-(4-morpholinyl)ethyl]-4-(trifluoromethyl)-N-[1-[3-(trifluoromethyl)phenyl]ethyl]-5-thiazolecarboxamide;
(48) 2-[1-hydroxy-2-(4-methyl-1-piperazinyl)ethyl]-4-(trifluoromethyl)-N-[1-[3-(trifluoromethyl)phenyl]ethyl]-5-thiazolecarboxamide;
(49) 2-[1-hydroxy-2-(4-methyl-1-piperazinyl)ethyl]-N-[(1S)-1-[3-(4-morpholinyl)phenyl]ethyl]-4-(trifluoromethyl)-5-thiazolecarboxamide;
(50) 2-[1-hydroxy-2-(4-methyl-1-piperazinyl)ethyl]-N-[(1S)-1-[3-(3-pyridinyl)phenyl]ethyl]-4-(trifluoromethyl)-5-thiazolecarboxamide;
(51) 2-[1-hydroxy-2-(1-piperidinyl)ethyl]-4-(trifluoromethyl)-N-[1-[3-(trifluoromethyl)phenyl]ethyl]-5-thiazolecarboxamide;
(52) 2-[1-hydroxy-2-(1-pyrrolidinyl)ethyl]-N-[1-[3-(trifluoromethoxy)phenyl]ethyl]-4-(trifluoromethyl)-5-thiazolecarboxamide;
(53) N-[1-[3-(dimethylamino)phenyl]ethyl]-2-[1-hydroxy-2-(1-pyrrolidinyl)ethyl]-4-(trifluoromethyl)-5-thiazolecarboxamide;
(54) 2-[1-hydroxy-2-(1-pyrrolidinyl)ethyl]-N-[(1S)-1-[3-(4-morpholinyl)phenyl]ethyl]-4-(trifluoromethyl)-5-thiazolecarboxamide;
(55) 2-[2-[(cyclopropylmethyl)propylamino]-1-hydroxyethyl]-4-(trifluoromethyl)-N-[1-[3-(trifluoromethyl)phenyl]ethyl]-5-thiazolecarboxamide; and
(56) 2-[2-(4-acetyl-1-piperazinyl)-1-hydroxyethyl]-4-(trifluoromethyl)-N-[1-[3-(trifluoromethyl)phenyl]ethyl]-5-thiazolecarboxamide;
and pharmaceutically acceptable salts and solvates of these compounds.

Synthetic Methods

The general procedures used to synthesize intermediates and the compounds of Formula I are illustrated in Reaction Scheme 1–2 and are described in detail in the Specific Embodiments section. Reasonable variations of the described procedures, which would be evident to one skilled in the art, are intended to be within the scope of the present invention.

As illustrated in Scheme 1, 2-Bromothiazole IV is coupled with vinyltributyltin under Stille reaction conditions to form vinyl thiazole III. Treatment of III directly with various amines of Formula $HNR^1R^2$ provides a variety of aminoethylthiazoles of structure IIa. Hydrolysis of the ester moiety of IIa followed by amination provides phenylalky lamide compounds of structure Ia, which represent a subgenus of Formula I compounds.

Alternatively, III can be epoxidized with potassium peroxymonosulfate (OXONE) followed by treatment with an amine of Formula $HNR^1R^2$ to form aminoethylthiazoles of structure IIb. Hydrolysis of the ester moiety of IIb followed by amination in the same manner as that for converting IIa provides phenylalkylamide compounds of structure Ib, which represent a second subgenus of Formula I compounds.

Scheme 1

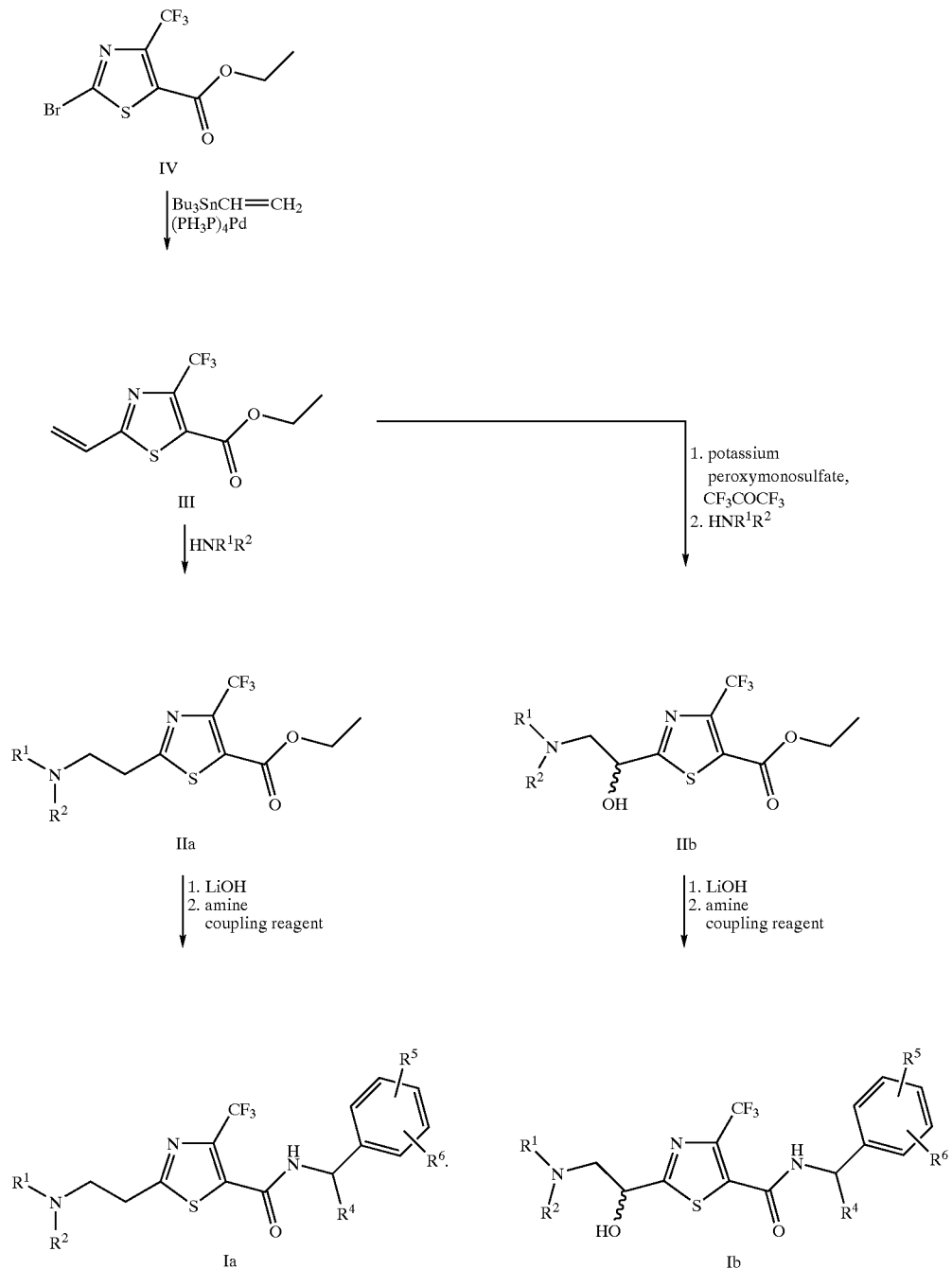

Scheme 2 illustrates a method for preparing other compounds of Formula I. Vinyl thiazole III can be converted to aldehyde IIc by ozonolysis. Reductive amination generates compounds of structure IId. Transformation of the ester moiety into an amide as described above produces Formula Ic compounds.

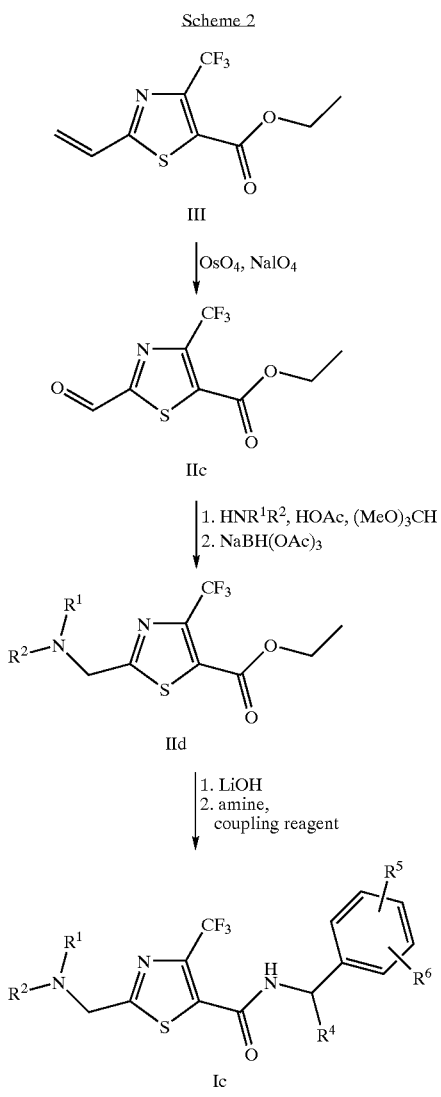

Biological Methods

KCNQ Potassium ($K^+$) channels are structurally and functionally diverse families of $K^+$-selective channel proteins which are ubiquitous in cells, indicating their central importance in regulating a number of key cell functions [Rudy, B., Neuroscience, 25: 729–749 (1988)]. While widely distributed as a class, $K^+$ channels are differentially distributed as individual members of this class or as families. [Gehlert, D. R., et al., Neuroscience, 52: 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the KCNQ family exemplified by KCNQ2, KCNQ2/3 heteromultimers, and KCNQ5, is regulated by transmembrane voltage and plays a potentially important role in the regulation of neuronal excitability [Biervert, C., et al., Science, 279: 403–406 (1998); Lerche, C. et al., J. Biol. Chem. 275:22395–22400 (2000); Wang, H. et al., Science, 282:1890–1893 (1998)].

An opener of KCNQ channels, such as the KCNQ2 and KCNQ2/3 channel opener retigabine, exerts its cellular effects by increasing the open probability of these channels [Main J., Mol Pharmacol 58(2):253–62 (2000); Wickenden, A. et al., Mol. Pharm. 58:591–600 (2000)]. This increase in the opening of individual KCNQ channels collectively results in the hyperpolarization of cell membranes, particularly in depolarized cells, produced by significant increases in whole-cell KCNQ-mediated conductance.

Thallium Flux Assay for KCNQ Channel Openers.

The thallium assay is a modification of that published by Weaver and is referenced in its entirety (Weaver, C. D. WO 02/31508, 2002).

Approximately 20,000 cells/well of an HEK-293 cell line stably transfected with one of the members of the KCNQ family were plated into clear-bottom, black-walled, poly-D-lysine coated, 384 well assay plates in 20 µl/well of low chloride plating medium. Low chloride plating medium was composed of the following: sodium gluconate, 109 mM; potassium gluconate, 5.4 mM; hemi-calcium gluconate, 3.6 mM; magnesium sulfate, 0.8 mM; sodium bicarbonate, 26.2 mM; sodium phosphate monobasic, 1.2 mM; glutamine, 2 mM; glucose, 5 mM; 4-(2-hydroxyethyl)-1-piperazineethanesulfonic acid (HEPES) (pH 7.3) 10 mM, MEM vitamin solution (10× concentration of vitamins, Gibco/LifeTechnologies 11120–052) and MEM amino acid solution (1× concentration of amino acids, Gibco/LifeTechnologies 11130–051).

Following overnight incubation in a 5% $CO_2$ incubator at 37° C., the cells in the plates were loaded with 20 µl/well of a dye loading solution containing the commercially available thallium-sensitive fluorescent dye BTC-AM, the acetomethoxy ester of BTC (see U.S. Pat. No. 5,501,980) (2 µM) and pluronic acid F-127 (Molecular Probes P 6867) (0.02% w/v) in chloride free assay buffer. Chloride free assay buffer was composed of the following: sodium gluconate, 140 mM; potassium gluconate, 2.5 mM; hemi-calcium gluconate, 6 mM; hemi-magnesium gluconate, 2 mM; glucose, 5 mM; HEPES (pH 7.3), 10 mM.

Following incubation in the dye loading solution for from 45–90 min at room temperature, the dye loading solution was removed by aspiration and replaced with 40 µl/well of chloride free assay buffer.

Prior to addition to cell plates, test compound and standard compounds were dissolved in DMSO to 3 mM concentration. Compounds were then diluted from the 3 mM stock to 100-fold over the final assay concentration in DMSO. Finally, compounds in DMSO were diluted from 100-fold over the final assay concentration to 5-fold over the final assay concentration in chloride free assay buffer.

Ten µl/well of compounds at 5-fold over the final assay concentration were then added to the cell plates. This represents a 1:5 dilution, yielding the final test concentration. The wells used for test compounds were A1-P20. Wells A21-P22 contained a standard opener and a maximally efficacious concentration (positive control). Wells A23-P24 contained chloride free assay buffer containing 1% DMSO (negative control).

Following addition of test compounds, the plates were loaded onto the Molecular Devices FLIPR. The 488 nm line of the argon laser was used to excite the BTC and the emission filter was a 540(+/−30) nm. Images were collected at 1 Hz. Ten seconds of baseline were collected and then the FLIPR was used to add 13 μl/well of a stimulus buffer composed of 7.5 mM Tl$_2$SO$_4$ in chloride free assay buffer. Images were collected for an additional 60 seconds.

For data analysis, the amplitude of the average of the negative controls was subtracted from all wells. The amplitudes of the test compounds were then compared to the value of four standard deviations of the negative control wells. The lowest concentration of a test compound sufficient to generate a signal amplitude greater than or equal to four standard deviations from the amplitude of the negative controls was defined as the minimal active concentration.

For generating EC$_{50}$ values, compounds were serially diluted in 1:3 volume increments to produce a 10 point concentration series. EC$_{50}$ values were calculated by fitting the resulting amplitudes to a single-site logistic equation. EC$_{50}$ was defined as the concentration of test compound required to yield 50% of the maximal response. Maximal response (Maximal opening) was the largest signal amplitude divided by the negative control amplitude generated by any concentration of a test compound.

Table 1 describes the effect of representative Formula I compounds on KCNQ channels. Example numbers refer to the examples described in the specific embodiments section. Examples 62 and 63 refer to 2-[2-(diethylamino)ethyl]-4-(trifluoromethyl)-N-[1-[3-(trifluoromethoxy)phenyl]ethyl]-5-thiazolecarboxamide and 2-[2-(4-thiomorpholinyl)ethyl]-4-(trifluoromethyl)-N-[1-[3-(trifluoromethyl)phenyl]ethyl]-5-thiazolecarboxamide.

TABLE 1

| Example | Structure | Min conc. response (μM) | EC$_{50}$ (μM) |
|---|---|---|---|
| 8 | morpholinyl-ethyl-2-[4-(trifluoromethyl)thiazol-5-yl]-C(=O)-NH-CH(CH$_3$)-(3-pyridin-3-yl-phenyl) | 10 | + |
| 9 | pyrrolidinyl-ethyl-2-[4-(trifluoromethyl)thiazol-5-yl]-C(=O)-NH-CH(CH$_3$)-(3-NMe$_2$-phenyl) | 10 | + |
| 10 | pyrrolidinyl-ethyl-2-[4-(trifluoromethyl)thiazol-5-yl]-C(=O)-NH-CH(CH$_3$)-(3-CF$_3$-phenyl) | 30 | + |
| 11 | (furan-2-yl-methyl)(Me)N-ethyl-2-[4-(trifluoromethyl)thiazol-5-yl]-C(=O)-NH-CH(CH$_3$)-(3-morpholinyl-phenyl) | 30 | + |
| 12 | (furan-2-yl-methyl)(Me)N-ethyl-2-[4-(trifluoromethyl)thiazol-5-yl]-C(=O)-NH-CH(CH$_3$)-(3-pyridin-3-yl-phenyl) | 3 | +++ |
| 13 | pyrrolidinyl-ethyl-2-[4-(trifluoromethyl)thiazol-5-yl]-C(=O)-NH-CH(CH$_3$)-(3-OCF$_3$-phenyl) | 10 | + |

TABLE 1-continued

| Example | Structure | Min conc. response (μM) | EC$_{50}$ (μM) |
|---|---|---|---|
| 14 | 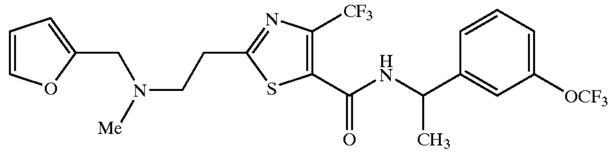 | 3 | +++ |
| 15 | 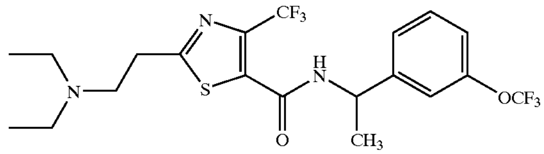 | 0.3 | ++ |
| 16 | 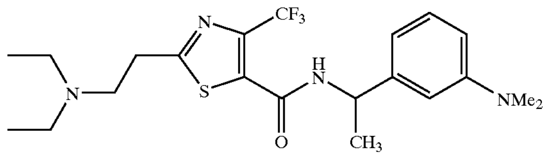 | 0.3 | + |
| 17 | 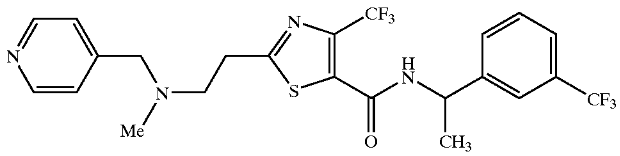 | 3 | + |
| 18 | 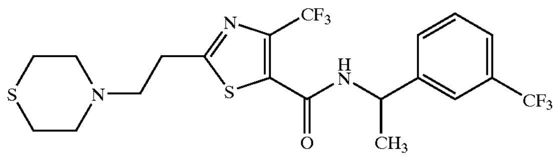 | 3 | ++ |
| 19 | 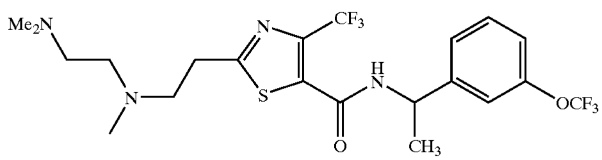 | 3 | + |
| 20 | 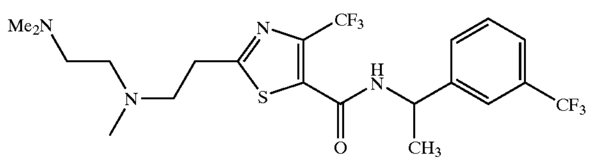 | 30 | + |
| 21 | 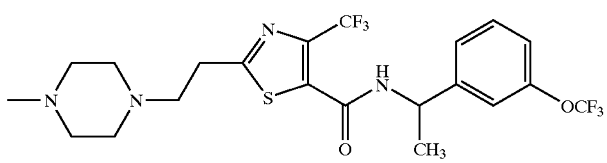 | 0.3 | + |
| 22 | 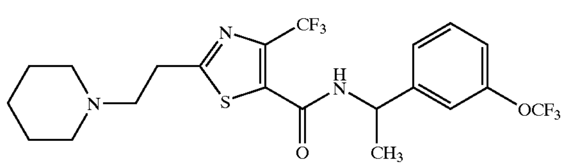 | 0.3 | ++ |

TABLE 1-continued

| Example | Structure | Min conc. response (μM) | EC50 (μM) |
|---|---|---|---|
| 23 | 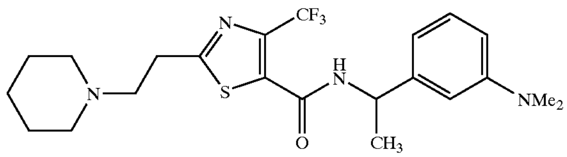 | 0.3 | + |
| 24 | 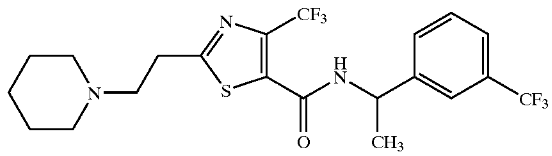 | 0.3 | + |
| 25 | 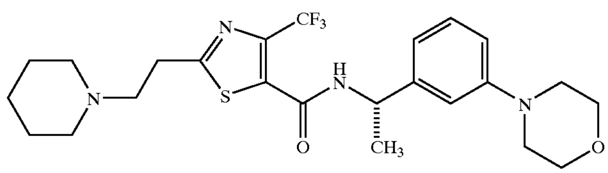 | 3 | + |
| 26 | 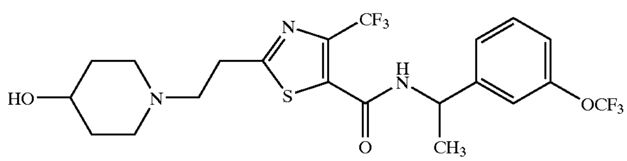 | 10 | + |
| 27 | 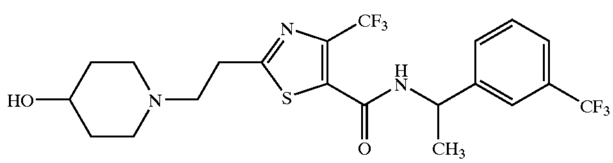 | 30 | + |
| 28 | 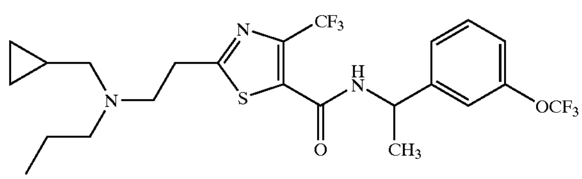 | 0.3 | +++ |
| 29 | 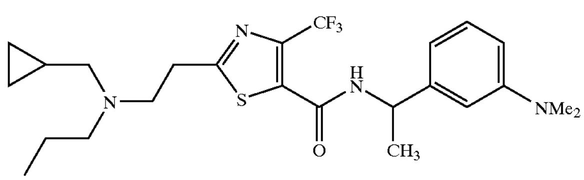 | 3 | + |
| 30 | 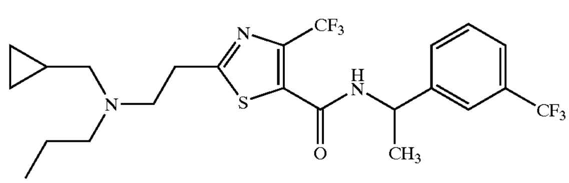 | 3 | +++ |

TABLE 1-continued

| Example | Structure | Min conc. response ($\mu M$) | EC$_{50}$ ($\mu M$) |
|---------|-----------|------------------------------|---------------------|
| 31 | 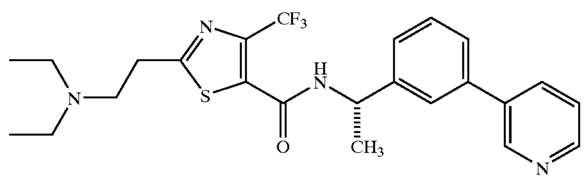 | 0.3 | + |
| 32 | 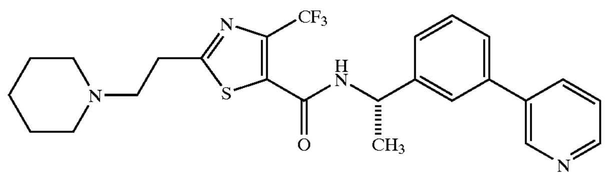 | 3 | + |
| 33 | 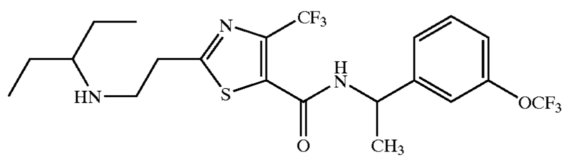 | | + |
| 34 | 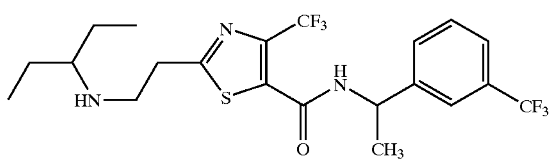 | 3 | + |
| 35 | 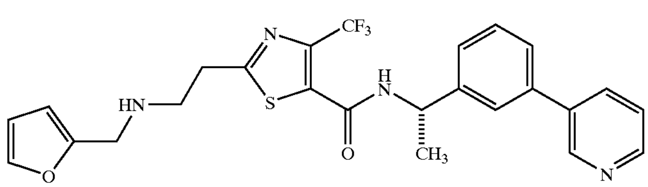 | 10 | + |
| 36 | 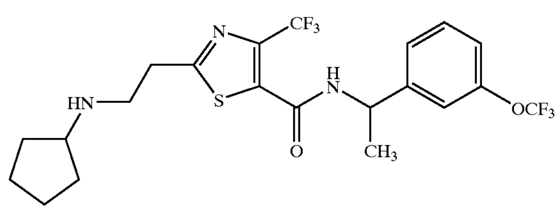 | 30 | + |
| 37 | 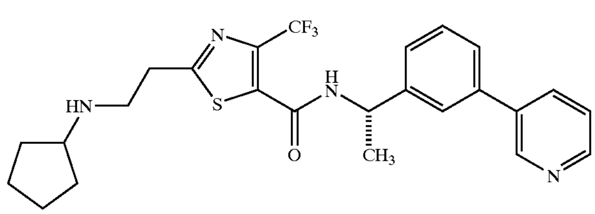 | 30 | + |
| 38 | 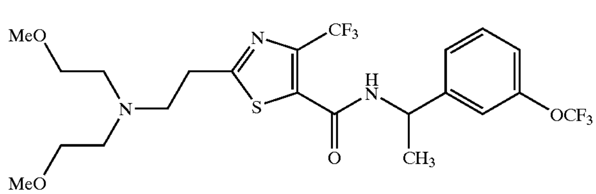 | 3 | + |

TABLE 1-continued

| Example | Structure | Min conc. response (μM) | EC$_{50}$ (μM) |
|---|---|---|---|
| 39 | 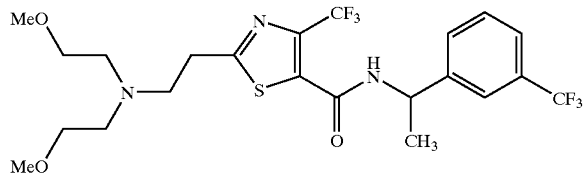 | 3 | + |
| 40 | 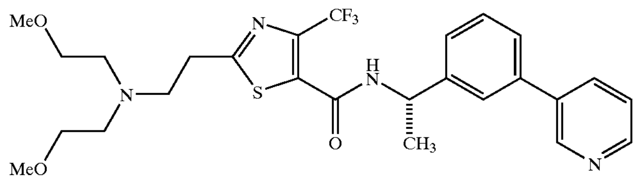 | 30 | ++ |
| 41 | 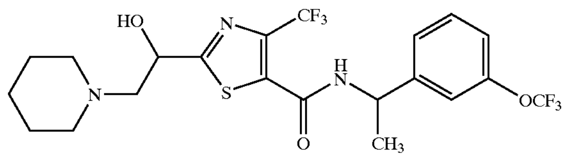 | 30 | + |
| 42 | 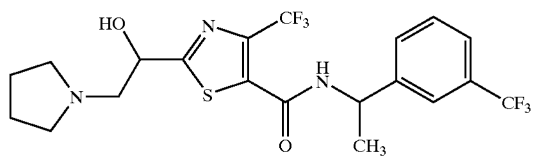 | 3 | ++ |
| 43 | 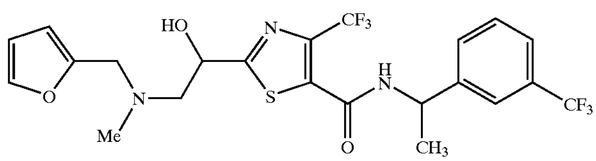 | 3 | ++ |
| 44 | 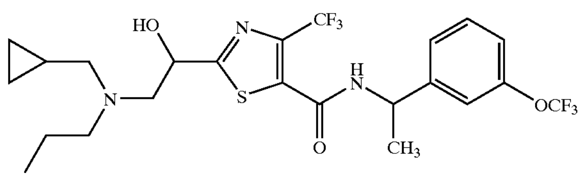 | 3 | ++ |
| 45 | 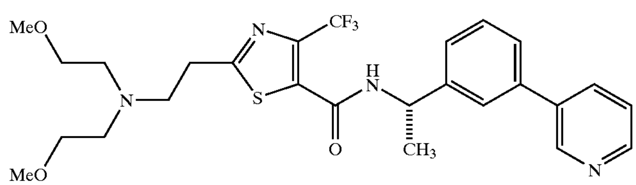 | 3 | na |
| 46 | 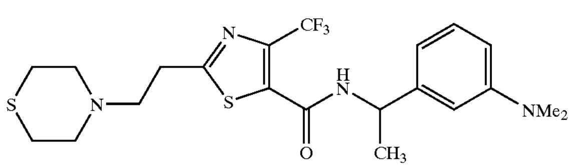 | 3 | na |

TABLE 1-continued

| Example | Structure | Min conc. response (μM) | EC$_{50}$ (μM) |
|---|---|---|---|
| 47 | 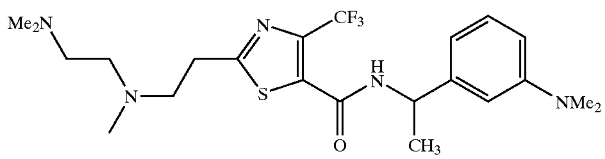 | 0.3 | na |
| 48 | 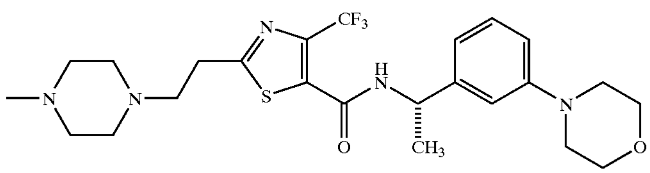 | 3 | na |
| 49 | 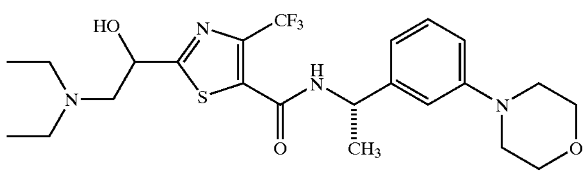 | 30 | na |
| 50 | 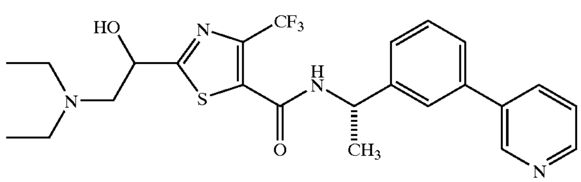 | 0.3 | na |
| 51 | 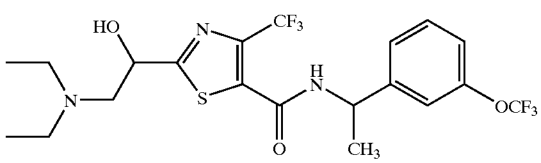 | 0.3 | na |
| 52 | 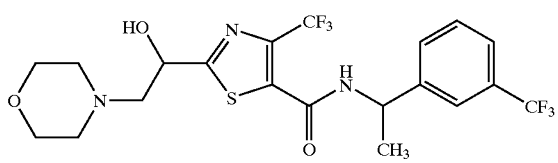 | 10 | na |
| 53 | 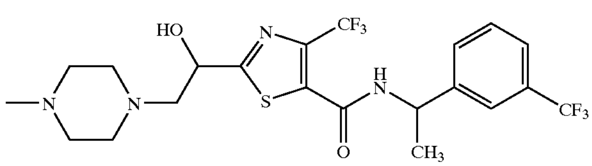 | 30 | na |
| 54 | 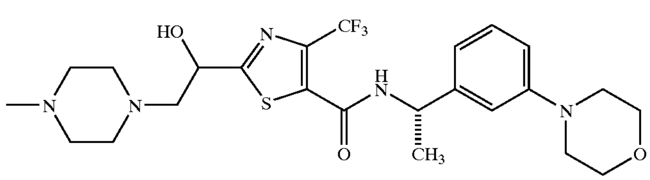 | 0.3 | na |

TABLE 1-continued

| Example | Structure | Min conc. response ($\mu$M) | EC$_{50}$ ($\mu$M) |
|---|---|---|---|
| 55 | 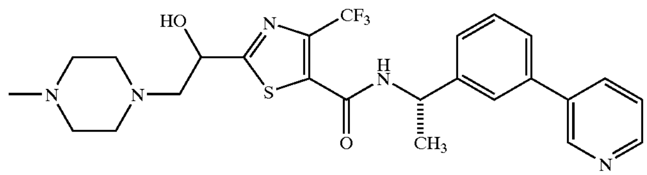 | 0.3 | na |
| 56 | 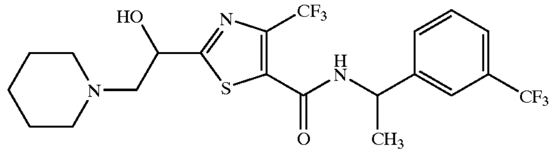 | 30 | na |
| 57 | 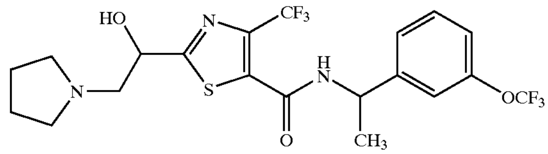 | 3 | na |
| 58 | 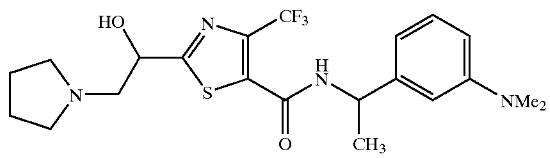 | 0.3 | na |
| 59 | 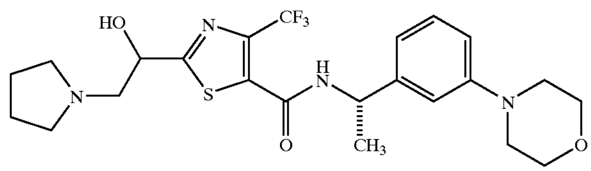 | 30 | na |
| 60 | 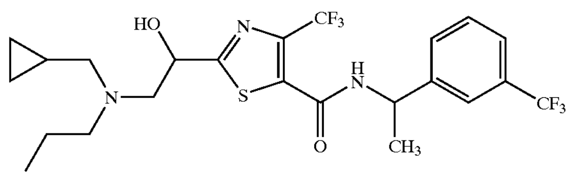 | 3 | na |
| 61 | 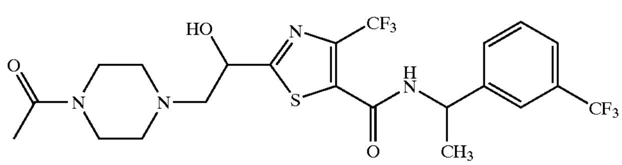 | 10 | na |

EC$_{50}$ values: +++ = <50 nM, ++ = 50–1000 nM, + = 1000–20000 nM.

Examples 8 and 11 were verified in a patch-clamp assay measuring the effect of compounds on the current of KCNQ channels.

KCNQ Patch-clamp. Whole-cell patch-clamp recordings were made from an HEK 293 stable cell line expressing mKCNQ2 channels, maintained in culture for 1–2 days. Patch pipettes had initial resistances of 2.5–4 M$\Omega$. Currents were recorded with an EPC-9 amplifier (HEKA, Lambrecht, Germany) controlled with software (Pulse, HEKA) run on a standard lab PC. Series resistance compensation was used during current recording, and set at 80%. The series resistance (R) and cell capacitance (C) were determined electronically by subtracting the capacitive currents at the onset and offset of a 5 mV voltage step. The cancellation of whole-cell capacitive transients was virtually complete in all cells. Analog current signals were low-pass filtered at 2.9 kHz using a four-pole Bessel filter –3 dB) and stored on a local network server computer at a sampling rate of 1.5 kHz. All recordings were performed at room temperature (20–22° C.). The pipette solution contained (mM):KCl, 150; CaCl$_2$, 2.5; EGTA, 5; MgCl$_2$, 1; HEPES, 10; pH to 7.3 with KOH, and Osmolality of 290–300 mOsm. The extracellular solution contained (mM): NaCl, 140; KCl, 2.5; CaCl$_2$, 2.5; MgCl$_2$, 1; glucose, 10; HEPES, 10; pH to 7.3 with NaOH, and Osmolality of 365–310 mOsm.

For analysis of agents effects on mKCNQ2 currents, the raw current records were displayed on the digital oscilloscope of the Pulse software application. Concentration response data were generated by measuring the difference in the steady-state amplitude of current in the presence of compound at the end of a 600 ms voltage-clamp step from a holding potential of −80 mV. The concentration-response data were fitted with Hill-type equations:

$$I=I_{max}/(1+EC_{50}/[A]^{nH}),$$

where I is the steady-state current at a given concentration of agonist [A]; and $I_{max}$, $EC_{50}$ and nH are parameters estimated from the curve fit. In some cases the concentration-response data were fitted with equations consisting of the sum of two Hill-type components. Current-voltage (I/V) relationships for agonist-evoked currents were obtained by performing 600 ms voltage steps (−110 mV to +40 mV) in the absence and presence of agonist. The $EC_{50}$ example 15 was 3.56 μM; the $EC_{50}$ of example 18 was 1.23 μM.

Pharmaceutical Composition and Methods of Treatment

Another aspect of this invention includes pharmaceutical compositions comprising at least one compound of Formula I in combination with a pharmaceutical adjuvant, carrier or diluent.

A further aspect of this invention relates to a method of treatment or prevention of disorders responsive to opening of KCNQ potassium channels in a mammal in need thereof, which comprises administering to said mammal a therapeutically effective amount of a compound of Formula I. The compounds of Formula I should be useful in the treatment of treatment of migraine or a migraine attack, cluster headaches, bipolar disorder, convulsions, mania, acute mania, epilepsy, anxiety, depression, schizophrenia, functional bowel disorders, stroke, traumatic brain injury, multiple sclerosis, neurodegenerative disorders or alleviating pain such as musculoskeletal pain, post operative pain, surgical pain, inflammatory pain, neuropathic pain such as diabetic neuropathy and pain associated with cancer and fibromyalgia.

For therapeutic use, the compounds of Formula I will normally be administered as pharmaceutical compositions comprising as an active ingredient at least one compound in association with a pharmaceutically acceptable solid or liquid carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. If a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Aerosol compositions can be formed with pharmaceutically accepted propellants. The pharmaceutical compositions are prepared by conventional techniques and are normally formulated in unit doses. The unit dose depends on the composition and can range from about 0.01 mg to about 1000 mg. Some unit doses for solid compositions are 1 mg, 10, mg, 100 mg, and 1000 mg. Some unit doses for liquid compositions are 0.01 mg/mL, 0.1 mg/mL, 1 mg/mL, 10 mg/mL, and 100 mg/mL.

A suitable dose of a compound of Formula I or a related pharmaceutical composition for a mammal, including man, is about 0.01 mg/kg to about 100 mg/kg body weight daily of active ingredient. For parenteral administration, the dose may be in the range of about 0.1 mg/kg to about 10 mg/kg body weight for intravenous administration. For oral administration, the dose may be in the range about 0.1 mg/kg to about 100 mg/kg body weight. The active ingredient can be administered continuously or in equal doses from one to four times a day. Usually a small dose is administered, and the dosage is gradually increased until the optimal dosage for the patient is determined. The specific dosing regimen, however, must be carefully monitered and adjusted using sound medical judgement.

DESCRIPTION OF SPECIFIC EMBODIMENTS

Unless otherwise stated, solvents and reagents were used directly as obtained from commercial sources, and reactions were performed under a nitrogen atmosphere. Flash chromatography was conducted on Silica gel 60 (0.040–0.063 particle size; EM Science supply). $^1$H NMR spectra were recorded on a Bruker DRX-500f at 500 MHz; a Bruker DPX-300B at 300 MHz; or a Varian Gemini 300 at 300 MHz. The chemical shifts were reported in ppm on the δ scale relative to δ TMS=0. The following internal references were used for the residual protons in the following solvents: CDCl$_3$ ($\delta_H$ 7.26), CD$_3$OD ($\delta_H$ 3.30) and DMSO-d$_6$ ($\delta_H$ 2.50). Standard acronyms were employed to describe the multiplicity patterns: s (singlet), d (doublet), t (triplet), q (quartet), quint (quintuplet), m (multiplet), br (broad), app (apparent). The coupling constant (J) is in hertz. LC/MS was performed on a Shimadzu LC-10AS liquid chromatograph using a SPD-10AV UV-VIS detector with Mass Spectrometry data determined using a Micromass LC Platform in positive electrospray ionization mode (ESI+). Mass Spectrometry (MS) data was obtained using a standard flow injection technique on a Micromass LC Platform in positive electrospray ionization mode (ESI+) unless otherwise noted. High resolution mass spectrometry (HRMS) data was obtained using a standard flow injection technique on a Finnigan MAT 900 mass spectrometer in electrospray ionization (ESI) mode. The analytical reverse phase HPLC method is as follows unless otherwise noted: Method: 3 min run is 2 min gradient from 100% A to 100% B followed by 1 min at 100% B; solvent A: 10% MeOH/90% H$_2$O/0.1% TFA; solvent B: 90% MeOH/10% H$_2$O/0.1% TFA; Column: XTERRA 3.0×50 mm S7. Preparative reverse phase HPLC was performed on a Shimadzu LC-8A automated preparative HPLC system with detector (SPD-10AV UV-VIS) wavelength and solvent systems (A and B) the same as above except where otherwise noted.

EXAMPLE 1

Preparation of Intermediate IV

2-Amino-4-Trifluoromethyl-thiazole-5-carboxylic acid ethyl ester. To a solution of ethyl 2-chloro-4,4,4- trifluoroacetoacetate (50.0 g, 230 mmol) in ethanol (250 mL) was added thiourea (17.5 g, 230 mmol). The resulting mixture was heated at reflux for 3 h, at which time TLC indicated a complete reaction. The mixture was concentrated in vacuo, and the residue dissolved in ether. The organic layer was successively washed with aqueous sodium bicarbonate, and brine, then dried over magnesium sulfate and concentrated in vacuo. The resulting solid was recrystalized with ethyl acetate and hexanes to give white crystals (41.64 g, 75% yield). $^1$H NMR (MeOD-d4, 300 MHz): δ 4.26 (q, J=7.1 Hz, 2H), 1.31 (t, J=7.1 Hz, 3H).

2-Bromo-4-Trifluoromethyl-thiazole-5-carboxylic acid ethyl ester (IV). To a solution of the aminothiazole (40.0 g, 167 mmol) in 48% HBr (300 mL) at 0° C. was added a 0° C. solution of sodium nitrite (17.0 g, 250 mmol) in water (200 mL) dropwise over 1 h. The mixture was stirred at 0° C. for an additional 0.5 h, at which time a 0° C. solution of CuBr (23.9 g, 167 mmol) in 48% HBr (200 mL) over 0.5 h. The mixture was stirred for an additional 0.5 h at 0° C., then for 2 h at room temperature. The mixture was then extracted three times with methylene chloride. The combined organic extracts were then dried over magnesium sulfate, filtered, and concentrated in vacuo. The product was purified by chromatography (SiO2, Hexane to 2.5% EtOAc/Hexane) to yield pure IV (47.0 g, 93% yield). $^1$H NMR (CDCl$_3$, 300 MHz): δ 4.40 (q, J=7.1 Hz, 2H), 1.38 (t, J=7.1 Hz, 3H).

EXAMPLE 2

Preparation of Intermediates of Formula III

4-Trifluoromethyl-2-vinyl-thiazole-5-carboxylic acid ethyl ester (III). To a solution of thiazole IV (17.4 g, 57.3 mmol) in toluene (150 mL) was added tetrakis (triphenylphosphine)palladium(0) (1.32 g, 1.14 mmol), tributyl(vinyl)tin (18.4 mL, 63.0 mmol), and 2,6-di-t-butyl-4-methyl phenol (catalytic). This mixture was stirred at 120° C. in a sealed tube for 25 min. The mixture was then allowed to come to 25° C. Ethyl acetate (250 mL) was added and the mixture was washed with 1 N aqueous NaOH (2×150 mL), saturated aqueous NaCl (1×150 mL), dried over MgSO$_4$ and concentrated in vacuo to give a brown oil. Purification by flash chromatography (silica, 0–10% ethyl acetate/hexane) gave the 2-vinyl thiazole III (11.0 g, 76%) as a yellow oil. $^1$H NMR (CDCl$_3$, 300 MHz): δ 6.88 (dd, J=11.0, 17.6 Hz, 1H), 6.20 (d, J=17.6 Hz, 1H), 5.74 (d, J=11.0 Hz, 1H), 4.38 (q, J=7.2 Hz, 2H), 1.37 (t, J=7.1 Hz, 3H).

EXAMPLE 3

Preparation of Intermediates of Formula IIa

General procedure for amination of intermediate III into intermediate IIa. To a solution of 2-vinyl thiazole III (400 mg, 1.59 mmol) in ethanol (4 mL) was added amine (167 μL, 1.91 mmol). This mixture was stirred at 25° C. for 1 h. The mixture was then concentrated in vacuo. Purification by flash chromatography (silica, 0–10% methanol/chloroform) gave thiazole IIa.

EXAMPLE 4

2-(2-Morpholin-4-yl-ethyl)-4-trifluoromethyl-thiazole-5-carboxylic acid ethyl ester. Prepared according to the method of example 3. Isolated as a brown oil (50%). $^1$H NMR (CDCl$_3$, 300 MHz): δ 4.38 (q, J=7.2 Hz, 2H), 3.80 (t, J=4.8 Hz, 4H), 3.18 (t, J=6.4 Hz, 2H), 2.72 (t, J=6.2 Hz, 2H),2.55 (t, J=4.4 Hz, 4H), 1.37 (t, J=7.0 Hz, 3H).

EXAMPLE 5

Preparation of Intermediates of Formula IIb

General procedure for converting intermediate III into intermediates of structure IIb. To a solution of 2-vinyl thiazole III (5.14 g, 20.5 mmol) in acetonitrile (150 mL) was added 4×10$^{-4}$ M aqueous NaEDTA (100 mL). This mixture was cooled to 0° C. and trifluoroacetone was added. A mixture of solid sodium bicarbonate (13.3 g, 158.7 mmol) and solid oxone (63 g, 102.4 mmol) was then added portionwise over 1 h. After the addition was complete, the mixture was stirred at 0° C. for an additional 30 min. The mixture was quenched with water (250 mL) and extracted with CH$_2$Cl$_2$ (3×150 mL). The combined organic extracts were washed with saturated aqueous NaCl (1×150 mL), dried over MgSO$_4$, and concentrated in vacuo. Purification by flash chromatography (silica, 0–10% methanol/chloroform) gave the epoxide (3.914 g, 72%) as a white solid.

To a solution of 2-oxiranyl-4-trifluoromethyl-thiazole-5-carboxylic acid ethyl ester (390 mg, 1.46 mmol) in ethanol (4 mL) was added amine (1.75 mmol). This mixture was brought to reflux and stirred for 2 h. The mixture was then concentrated in vacuo. Purification of the resulting oil by flash chromatography (silica, 0–5% methanol/chloroform) gave thiazole IIb.

EXAMPLE 6

2-(2-Diethylamino-1-hydroxy-ethyl)-4-trifluoromethyl-thiazole-5-carboxylic acid ethyl ester. Prepared by the method of example 5. Isolated as a yellow oil. $^1$H NMR (CDCl$_3$, 300 MHz): δ 7.37 (app d, J=1.8 Hz, 1H), 6.31 (dd, J=2.0, 2.7 Hz, 1H), 6.20 (d, J=3.3 Hz, 1H), 4.92 (dd, J=4.6, 9.0 Hz, 1H), 4.37 (q, J=7.2 Hz, 2H), 3.67 (AB q, J=8.8 Hz, Δv=14.3 Hz, 2H), 2.96 (dd, J=4.4, 12.8 Hz, 1H), 2.68 (dd, J=9.2, 12.8 Hz, 1H), 2.34 (s, 3H), 1.36 (t, J=7.2 Hz, 3H).

EXAMPLE 7

Preparation of Formula I Compounds

General procedure for converting intermediate II into compounds of Formula I. To a solution of thiazole II (0.8 mmol) in THF (2 mL) was added 1 N aqueous LiOH (1 mL). This mixture was heated to reflux and stirred vigorously for 1 h. The mixture was allowed to come to 25° C. 1 N aqueous HCl (1 mL) was added and the resulting mixture was concentrated in vacuo. The crude residue was used as is.

To a solution of the resulting carboxylic acid (0.145 mmol) in DMF (1 mL) was added DEPBT (54 mg, 0.18 mmol). A solution of [3-(1-Amino-ethyl)-phenyl]-dimethyl-amine (24 mg, 0.145 mmol) in DMF (0.5 mL) was then added, followed by Et$_3$N (81 μL, 0.58 mmol). This mixture was stirred at 25° C. for 18 h. The reaction mixture was filtered and applied directly to a preparatory HPLC column for purification (C18, 10–100% methanol/water/0.1% trifluoroacetic acid). The resulting residue was taken up in methanol (3 mL) and applied to an SAX column (United Chemical Technologies CHQAX12M6) having hydroxide as the counter ion. The product was eluted with methanol (10 mL). The methanol solution was concentrated in vacuo to give thiazole I.

Compounds which needed further purification were purified by flash chromatography (silica, 0–10% methanol/chloroform).

Examples of Formula I Compounds

EXAMPLE 8

2-[2-[(4-morpholinyl)ethyl]-N-[1-[3-(3-pyridinyl) phenyl]ethyl]-4-(trifluoromethyl)-5-thiazolecarboxamide. $^1$H NMR (CDCl$_3$, 300 MHz): δ 8.80 (s, 1H), 8.57 (s, 1H), 7.85 (d, J=8.1 Hz, 1H), 7.53–7.35 (m, 5H), 6.52 (br d, J=7.0 Hz, 1H), 5.31 (app quint, J=7.1 Hz, 1H), 3.80–3.70 (m, 4H), 3.22–3.08 (m, 4H), 2.76–2.65 (m, 2H), 2.60–2.48 (m, 2H), 1.63 (d, J=6.9 Hz, 3H); LCMS (M+) 490, RT=0.773.

EXAMPLE 9

N-[1-[3-(dimethylamino)phenyl]ethyl]-2-[2-(1-pyrrolidinyl)ethyl]-4-(trifluoromethyl)-5-thiazolecarboxamide. $^1$H NMR (CDCl$_3$, 300 MHz): δ 7.26–7.17 (m, 1H), 6.70–6.61 (m, 3H), 6.35 (br d, J=7.3 Hz, 1H), 5.17 (app quint, J=7.1 Hz, 1H), 3.21 (t, J=6.9 Hz, 2H), 2.97–2.85 (m, 8H), 2.74–2.61 (m, 4H), 1.90–1.78 (m, 4H), 1.57 (d, J=6.9 Hz, 3H); LCMS (M+) 440, T=0.603.

EXAMPLE 10

2-[2-(1-pyrrolidinyl)ethyl]-4-(trifluoromethyl)-N-[1-[3-(trifluoromethyl)phenyl]ethyl]-5-thiazolecarboxamide. $^1$H NMR (CDCl$_3$, 300 MHz): δ 7.58–7.44 (m, 4H), 6.45 (br d, J=6.6 Hz, 1H), 5.25 (app quint, J=7.1 Hz, 1H), 3.18 (t, J=6.4 Hz, 2H), 2.86 (t, J=6.3 Hz, 2H), 2.70–2.58 (m, 4H), 1.88–1.74 (m, 4H), 1.58 (d, J=6.9 Hz, 3H); LCMS (M+) 465, RT=1.280.

EXAMPLE 11

2-[2-[(2-furanylmethyl)methylamino]ethyl]-N-[1-[3-(4-morpholinyl)phenyl]ethyl]-4-(trifluoromethyl)-5-thiazolecarboxamide. $^1$H NMR (CDCl$_3$, 300 MHz): δ 7.34 (dd, J=0.7, 1.8 Hz, 1H), 7.30–7.22 (m, 1H), 6.91–6.79 (m, 3H), 6.34–6.25 (m, 2H), 6.19 (d, J=2.9 Hz, 1H), 5.19 (app quint, J=7.1 Hz, 1H), 3.84 (t, J=4.8 Hz, 4H), 3.65 (s, 2H), 3.20–3.09 (m, 6H), 2.76 (t, J=6.6 Hz, 2H), 2.31 (s, 3H), 1.57 (d, J=6.9 Hz, 3H); LCMS (M+) 522, RT=0.993.

EXAMPLE 12

2-[2-[(2-furanylmethyl)methylamino]ethyl]-N-[1-[3-(3-pyridinyl)phenyl]ethyl]-4-(trifluoromethyl)-5-thiazolecarboxamide. $^1$H NMR (CDCl$_3$, 300 MHz): δ 8.81 (s, 1H), 8.58 (d, J=4.2 Hz, 1H), 7.86 (dt, J=1.9,7.9 Hz, 1H), 7.54–7.32 (m, 6H), 6.45 (d, 1H), 6.29 (m, 1H), 6.19 (m, 1H), 5.32 (m, 1H), 3.65 (s, 2H), 3.14 (t, J=6.6 Hz, 2H), 2.77 (t, J=6.3 Hz, 2H), 2.31 (s, 3H), 1.63 (d, J=6.9 Hz, 3H); LCMS (M+) 514, RT=0.877.

EXAMPLE 13

2-[2-(1-pyrrolidinyl)ethyl]-4-(trifluoromethyl)-N-[1-[3-(trifluoromethoxy)phenyl]ethyl]-5-thiazolecarboxamide. $^1$H NMR (CDCl$_3$, 300 MHz): δ 7.41–7.12 (m, 4H), 6.32 (br d, J=6.2 Hz, 1H), 5.24 (app quint, J=7.1 Hz, 1H), 3.15 (t, J=6.3 Hz, 2H), 2.82 (t, J=6.3 Hz, 2H), 2.64–2.54 (m, 4H), 1.86–1.75 (m, 4H), 1.57 (d, J=6.9 Hz, 3H); LCMS (M+) 481, RT=1.320.

EXAMPLE 14

2-[2-[(2-furanylmethyl)methylamino]ethyl]-4-(trifluoromethyl)-N-[1-[3-(trifluoromethoxy)phenyl]ethyl]-5-thiazolecarboxamide. $^1$H NMR (CDC$_3$, 300 MHz): δ 7.38–7.13 (m, 5H), 6.31–6.18 (m, 3H), 5.25 (app quint, J=7.1 Hz, 1H), 3.64 (s, 2H), 3.13 (t, J=6.3 Hz, 2H), 2.76 (d, J=6.3 Hz, 2H), 2.31 (s, 3H), 1.57 (d, J=6.9 Hz, 3H); LCMS (M+) 521, RT=1.380.

EXAMPLE 15

2-[2-[(2-diethylamino)ethyl]-4-(trifluoromethyl)-N-[1-[3-(trifluoromethoxy)phenyl]ethyl]-5-thiazolecarboxamide. $^1$H NMR (CDCl$_3$, 300 MHz): δ 7.4–7.1 (m, 4H), 6.36 (br d, J=6.6 Hz, 1H), 5.23 (app quint, J=7.1 Hz, 1H), 3.20 (t, J=6.2 Hz, 2H), 2.81 (t, J=6.2 Hz, 2H), 2.65 (q, J=7.2 Hz, 4H), 1.57 (d, J=7.0 Hz, 3H), 1.05 (t, J=7.1 Hz, 6H); LCMS (M+) 483, RT=1.393.

EXAMPLE 16

2-[2-(diethylamino)ethyl]-N-[1-[3-(dimethylamino)phenyl]ethyl]-4-(trifluoromethyl)-5-thiazolecarboxamide. $^1$H NMR (CDCl$_3$, 300 MHz): δ 7.27–7.17 (m, 1H), 6.7–6.61 (m, 3H), 6.31 (br d, J=5.9 Hz, 1H), 5.17 (app quint, J=7.1 Hz, 1H), 3.10 (t, J=6.4 Hz, 2H), 2.95 (s, 6H), 2.76 (t, J=6.4 Hz, 2H), 2.60 (q, J=7.2 Hz, 4H), 1.58 (d, J=6.6 Hz, 3H), 1.02 (t, J=7.1 Hz, 6H); LCMS (M+) 442, RT=0.613.

EXAMPLE 17

2-[2-[(4-pyridylmethyl)methylamino]ethyl]-4-(trifluoromethyl)-N-[1-[3-(trifluoromethyl)phenyl]ethyl]-5-thiazolecarboxamide. $^1$H NMR (CDCl$_3$, 300 MHz): δ 8.45 (d, J=5.9 Hz, 2H), 7.63–7.43 (m, 4H), 7.18 (d, J=5.9 Hz, 2H), 6.68 (br d, J=7.3 Hz, 1H), 5.28 (app quint, J=7.1 Hz, 1H), 3.61 (s, 2H), 3.10 (t, J=6.4 Hz, 2H), 2.84 (t, J=6.4 Hz, 2H), 2.58 (q, J=7.0 Hz, 2H), 1.61 (d, J=7.0 Hz, 3H), 1.03 (t, J=7.0 Hz, 3H); LCMS (M+) 530, RT=1.263.

EXAMPLE 18

2-[2-(4-thiomorpholinyl)ethyl]-4-(trifluoromethyl)-N-[1-[3-(trifluoromethyl)phenyl]ethyl]-5-thiazolecarboxamide. $^1$H NMR (CDCl$_3$, 300 MHz): δ 7.62–7.43 (m, 4H), 6.36 (br d, J=6.2 Hz, 1H), 5.28 (app quint, J=7.1 Hz, 1H), 3.13 (t, J=6.2 Hz, 2H), 2.84–2.75 (m, 4H), 2.75–2.64 (m, 6H), 1.60 (d, J=7.0 Hz, 3H); LCMS (M+) 497, RT=1.350.

EXAMPLE 19

2-[2-[[(3-dimethylamino)propyl]methylamino]ethyl]-N-[1-[3-(3-trifluoromethoxy)phenyl]ethyl]-4-(trifluoromethyl)-5-thiazolecarboxamide. $^1$H NMR (CDCl$_3$, 300 MHz): δ 7.40–7.20 (m, 4H), 7.11 (br d, J=6.6 Hz, 1H), 5.23 (app quint, J=7.1 Hz, 1H), 3.13 (t, J=6.2 Hz, 2H), 2.79 (t, J=6.2 Hz, 2H), 2.67–2.55 (m, 4H), 2.35 (s, 6H), 2.30 (s, 3H), 1.58 (d, J=7.0 Hz, 3H); LCMS (M+) 512, RT=1.227.

EXAMPLE 20

2-[2-[[(3-dimethylamino)propyl]methylamino]ethyl]-N-[1-[3-(3-trifluoromethyl)phenyl]ethyl]-4-(trifluoromethyl)-5-thiazolecarboxamide. $^1$H NMR (CDCl$_3$, 300 MHz): δ 7.65–7.40 (m, 4H), 7.14 (br s, 1H), 5.26 (app quint, J=7.1 Hz, 1H), 3.14 (t, J=6.4 Hz, 2H), 2.79 (t, J=6.4 Hz, 2H), 2.69–2.53 (m, 4H), 2.34 (s, 6H), 2.30 (s, 3H), 1.69 (d, J=7.0 Hz, 3H); LCMS (M+) 496, RT=1.183.

EXAMPLE 21

2-[2-(4-methyl-1-piperazinyl)ethyl]-N-[1-[3-(3-trifluoromethoxy)phenyl]ethyl]-4-(trifluoromethyl)-5-thiazolecarboxamide. $^1$H NMR (CDCl$_3$, 300 MHz): δ 7.42–7.08 (m, 4H), 6.38 (br d, J=7.0 Hz, 1H), 5.23 (app quint, J=7.1 Hz, 1H), 3.13 (t, J=6.2 Hz, 2H), 2.68 (t, J=6.4 Hz, 2H), 2.64–2.43 (m, 8H), 2.31 (s, 3H), 1.57 (d, J=7.0 Hz, 3H); LCMS (M+) 510, RT=1.307.

EXAMPLE 22

2-[2-(1-piperidinyl)ethyl]-N-[1-[3-(3-trifluoromethoxy)phenyl]ethyl]-4-(trifluoromethyl)-5-thiazolecarboxamide. $^1$H NMR (CDCl$_3$, 300 MHz): δ 7.42–7.10 (m, 4H), 6.34 (br d, J=6.6 Hz, 1H), 5.24 (app quint, J=7.1 Hz, 1H), 3.15 (t, J=6.4 Hz, 2H), 2.64 (t, J==6.2 Hz, 2H), 2.54–2.39 (m, 4H), 1.69–1.52 (m, 7H), 1.52–1.40 (m, 2H); LCMS (M+) 495, RT=1.353.

EXAMPLE 23

N-[1-[3-(dimethylamino)phenyl]ethyl]-2-[2-(1-piperidinyl)ethyl]-4-(trifluoromethyl)-5- thiazolecarboxamide. ¹H NMR (CDCl₃, 300 MHz): δ 7.26–7.18 (m, 1H), 6.71–6.62 (m, 3H), 5.17 (app quint, J=7.1 Hz, 1H), 3.15 (t, J=6.2 Hz, 2H), 2.95 (s, 6H), 2.65 (t, J=6.4 Hz, 2H), 2.55–2.40 (m, 4H), 1.69–1.53 (m, 7H), 1.52–1.41 (m, 2H); LCMS (M+) 455, RT=0.687.

EXAMPLE 24

2-[2-(1-piperidinyl)ethyl]-N-[1-[3-(3-trifluoromethyl)phenyl]ethyl]-4-(trifluoromethyl)-5-thiazolecarboxamide. ¹H NMR (CDCl₃, 300 MHz): δ 7.61–7.42 (m, 4H), 6.38 (br d, J=6.6 Hz, 1H), 5.27 (app quint, J=7.1 Hz, 1H), 3.14 (t, J=6.4 Hz, 2H), 2.63 (t, J=6.4 Hz, 2H), 2.54–2.40 (m, 4H), 1.69–1.53 (m, 7H), 1.53–1.40 (m, 2H); LCMS (M+) 479, RT=1.317.

EXAMPLE 25

N-[1-[3-(4-morpholinyl)phenyl]ethyl]-2-[2-(1-piperidinyl)ethyl]-4-(trifluoromethyl)-5-thiazolecarboxamide. ¹H NMR (CDCl₃, 300 MHz): δ 7.31–7.20 (m, 1H), 6.91–6.79 (m, 3H), 6.32 (br d, J=7.0 Hz, 1H), 5.18 (app quint, J=7.1 Hz, 1H), 3.84 (t, J=4.8 Hz, 4H), 3.19–3.09 (m, 6H), 2.64 (t, J=6.2 Hz, 2H), 2.54–2.40 (m, 4H), 1.69–1.52 (m, 7H), 1.52–1.41 (m, 2H); LCMS (M+) 496, RT=0.943.

EXAMPLE 26

2-[2-(4-hydroxy-1-piperidinyl)ethyl]-4-(trifluoromethyl)-N-[1-[3-(trifluoromethoxy)phenyl]ethyl]-5-thiazolecarboxamide. ¹H NMR (CDCl₃, 300 MHz): δ 7.46–7.09 (m, 4H), 6.37 (br d, J=5.5 Hz, 1H), 5.23 (app quint, J=7.1 Hz, 1H), 3.74 (s, 1H), 3.14 (t, J=6.2 Hz, 2H), 2.89–2.75 (m, 2H), 2.67 (t, J=5.9 Hz, 2H), 2.40–2.20 (m, 2H), 2.02–1.85 (m, 2H), 1.74–1.49 (m, 6H); LCMS (M+) 511, RT=1.353.

EXAMPLE 27

2-[2-(4-hydroxy-1-piperidinyl)ethyl]-4-(trifluoromethyl)-N-[1-[3-(trifluoromethyl)phenyl]ethyl]-5-thiazolecarboxamide. ¹H NMR (CDCl₃, 300 MHz): δ 7.62–7.41 (m, 4H), 6.41 (br d, J=6.2 Hz, 1H), 5.27 (app quint, J=7.1 Hz, H), 3.80–3.67 (m, 1H), 3.14 (t, J=6.2 Hz, 2H), 2.86–2.75 (m, 2H), 2.67 (t, J=6.2 Hz, 2H), 2.37–2.19 (m, 2H), 1.97–1.85 (m, 2H), 1.70–1.51 (m, 6H); LCMS (M+) 495, RT=1.313.

EXAMPLE 28

2-[2-[(cyclopropylmethyl)propylamino]ethyl]-N-[1-[3-(trifluoromethoxy)phenyl]ethyl]-4-(trifluoromethyl)-5-thiazolecarboxamide. ¹H NMR (CDCl₃, 300 MHz): δ 7.41–7.10 (m, 4H), 6.34 (br d, J=6.2 Hz, 1H), 5.23 (app quint, J=7.1 Hz, 1H), 3.15 (t, J=6.2 Hz, 2H), 2.91 (t, J=5.7 Hz, 2H), 2.59 (t, J=7.7 Hz, 2H), 2.46 (d, J=6.2 Hz, 2H), 1.61–1.42 (m, 5H), 0.93–0.81 (m, 4H), 0.55–0.45 (m, 2H), 0.15–0.05 (m, 2H); LCMS (M+) 523, RT=1.497.

EXAMPLE 29

2-[2-[(cyclopropylmethyl)propylamino]ethyl]-N-[1-[3-(dimethylamino)phenyl]ethyl]-4-(trifluoromethyl)-5-thiazolecarboxamide. ¹H NMR (CDCl₃, 300 MHz): δ 7.26–7.17 (m, 1H), 6.71–6.61 (m, 3H), 6.32 (br d, J=7.0 Hz, 1H), 5.17 (app quint, J=7.1 Hz, 1H), 3.15 (br t, 2H), 2.99–2.85 (m, 8H), 2.58 (br t, 2H), 2.45 (d, J=5.1 Hz, 2H), 1.62–1.43 (m, 5H), 0.93–0.80 (m, 4H), 0.56–0.45 (m, 2H), 0.15–0.05 (m, 2H); LCMS (M+) 482, RT=0.823.

EXAMPLE 30

2-[2-[(cyclopropylmethyl)propylamino]ethyl]-N-[1-[3-(trifluoromethyl)phenyl]ethyl]-4-(trifluoromethyl)-5-thiazolecarboxamide. ¹H NMR (CDCl₃, 300 MHz): δ 7.66–7.42 (m, 4H), 6.36 (br d, J=6.2 Hz, 1 H), 5.27 (app quint, J=7.1 Hz, 1H), 3.15 (br t, 2H), 2.90 (br t, 2H), 2.59 (br t, 2H), 2.45 (d, J=6.2 Hz, 2H), 1.67–1.41 (m, 5H), 0.98–0.78 (m, 4H), 0.60–0.42 (m, 2H), 0.20–0.03 (m, 2H); LCMS (M+) 507, RT=1.267.

EXAMPLE 31

2-[2-[(diethylamino]ethyl]-N-[1-[3-(3-pyridinyl)phenyl]ethyl]-4-(trifluoromethyl)-5-thiazolecarboxamide. ¹H NMR (CDCl₃, 300 MHz): δ 8.78 (d, J=1.83 Hz, 1H), 8.55 (dd, J=1.7, 4.9 Hz, 1H), 7.85 (dt, J=2.0, 7.7 Hz, 1H), 7.56–7.51 (m, 1H), 7.51–7.42 (m, 2H), 7.42–7.30 (m, 2H), 6.85 (br d, J=6.2 Hz, 1H), 5.30 (app quint, J=7.1 Hz, 1H), 3.25 (br t, 2H), 3.03 (br t, 2H), 2.81 (q, J=7.1 Hz, 4H), 1.62 (d, J=7.0 Hz, 3H), 1.13 (t, J=7.1 Hz, 6H); LCMS (M+) 476, RT=0.780.

EXAMPLE 32

2-[2-(1-piperidinyl)ethyl]-N-[1-[3-(3-pyridinyl)phenyl]ethyl]-4-(trifluoromethyl)-5-thiazolecarboxamide. ¹H NMR (CDCl₃, 300 MHz): δ 8.78 (d, J=2.2 Hz, 1H), 8.50 (dd, J=1.7, 4.9 Hz, 1H), 7.85 (dt, J=1.9, 7.9 Hz, 1H), 7.53 (s, 1H), 7.50–7.43 (m, 2H), 7.43–7.31 (m, 2H), 6.66 (br d, J=6.6 Hz, 1H), 5.30 (app quint, J=7.1 Hz, 1H), 3.17 (t, J=6.4 Hz, 2H), 2.71 (t, J=6.4 Hz, 2H), 2.60–2.46 (m, 4H), 1.70–1.57 (m, 7H), 1.53–1.38 (m, 2H); LCMS (M+) 488, RT=0.810.

EXAMPLE 33

2-[2-(3-pentylamino)ethyl]-N-[1-[3-(trifluoromethoxy)phenyl]ethyl]-4-(trifluoromethyl)-5-thiazolecarboxamide. ¹H NMR (CDCl₃, 300 MHz): δ 7.41–7.09 (m, 4H), 6.51 (br d, J=7.0 Hz, 1H), 5.21 (app quint, J=7.1 Hz, 1H), 3.17 (t, J=6.2 Hz, 2H), 3.01 (t, J=6.2 Hz, 2H), 2.64 (br s, 1H), 2.48 (quint, J=5.9 Hz, 1H), 1.55 (d, J=7.0 Hz, 3H), 1.47 (app quint, J=7.1 Hz, 4H), 0.88 (t, J=7.5 Hz, 6H); LCMS (M+) 497, RT=1.590.

EXAMPLE 34

2-[2-(3-pentylamino)ethyl]-N-[1-[3-(trifluoromethyl)phenyl]ethyl]-4-(trifluoromethyl)-5-thiazolecarboxamide. ¹H NMR (CDCl₃, 300 MHz): δ 7.59–7.41 (m, 4H), 6.54 (br d, J=7.0 Hz, 1H), 5.25 (app quint, J=7.1 Hz, 1H), 3.18 (t, J=6.2 Hz, 2H), 3.02 (t, J=6.0 Hz, 2H), 2.68 (br s, 1H), 2.49 (quint, J=5.9 Hz, 1H), 1.58 (d, J=7.0 Hz, 3H), 1.53–1.41 (m, 4H), 0.88 (t, J=7.3 Hz, 6H); LCMS (M+) 481, RT=1.540.

EXAMPLE 35

2-[2-[(2-furanylmethyl)amino]ethyl]-N-[1-[3-(3-pyridinyl)phenyl]ethyl]-4-(trifluoromethyl)-5-thiazolecarboxamide. ¹H NMR (CDCl₃, 300 MHz): δ 8.79 (d, J=1.8 Hz, 1H), 8.56 (dd, J=1.8, 4.8 Hz, 1H), 7.85 (dt, J=2.0, 8.0 Hz, 1H), 7.55–7.43 (m, 3H), 7.43–7.30n (m, 3H), 6.57 (br d, J=7.0 Hz, 1H), 6.3 (dd, J=2.0, 3.1 Hz, 1H), 6.18 (d, J=3.3 Hz, 1H), 5.30 (app quint, J=7.1 Hz, 1H), 3.81 (s, 2H), 3.12 (t, J=6.0 Hz, 2H), 2.99 (t, J=6.0 Hz, 2H), 1.96 (s, 1H), 1.62 (d, J=7.0 Hz, 3H); LCMS (M+) 500, RT=0.983.

EXAMPLE 36

2-[2-(cyclopentylamino)ethyl]-N-[1-[3-(trifluoromethoxy)phenyl]ethyl]-4-(trifluoromethyl)-5-thiazolecarboxamide. ¹H NMR (CDCl₃, 300 MHz): δ 7.42–7.08 (m, 4H), 6.66 (br d, J=6.6 Hz, 1H), 5.21 (app quint, J=7.1 Hz, 1H), 3.26–3.11 (m, 3H), 3.06 (t, J=6.4 Hz, 2H), 2.92 (br s, 1H), 1.94–1.79 (m, 2H), 1.79–1.63 (m, 2H), 1.63–1.50 (m, 5H), 1.50–1.36 (m, 2H); LCMS (M+) 495, RT=1.530.

EXAMPLE 37

2-[2-(3-pentylamino)ethyl]-N-[1-[3-(3-pyridinyl)phenyl]ethyl]-4-(trifluoromethyl)-5-thiazolecarboxamide. $^1$H NMR (CDCl$_3$, 300 MHz): δ 8.77 (d, J=1.8 Hz, 1H), 8.54 (dd, J=1.5, 4.8 Hz, 1H), 7.84 (dt, J=2.0, 8.2 Hz, 1H), 7.53 (s, 1H), 7.50–7.41 (m, 2H), 7.41–7.30 (m, 2H), 6.87 (br d, J=7.3 Hz, 1H), 5.28 (app quint, J=7.1 Hz, 1H), 3.26–3.141 (m, 3H), 3.11–2.88 (m, 3H), 1.94–1.77 (m, 2H), 1.77–1.64 (m, 2H), 1.61 (d, J=7.0 Hz, 3H), 1.57–1.36 (m, 4H); LCMS (M+) 488, RT=1.043.

EXAMPLE 38

2-[2-(cyclopentylamino)ethyl]-N-[1-[3-(trifluoromethoxy)phenyl]ethyl]-4-(trifluoromethyl)-5-thiazolecarboxamide. $^1$H NMR (CDCl$_3$, 300 MHz): δ 7.41–7.33 (m, 1H), 7.31–7.23 (m, 1H), 7.20–7.09 (m, 2H), 6.39 (br d, J=7.0 Hz, 1H), 5.24 (app quint, J=7.1 Hz, 1H), 3.45 (t, J=5.7 Hz, 4H), 3.28 (s, 6H), 3.11 (t, J=6.4 Hz, 2H), 2.93 (t, J=6.4 Hz, 2H), 2.78 (t, J=5.7 Hz, 4H), 1.57 (d, J=7.0 Hz, 3H); LCMS (M+) 543, RT=1.490.

EXAMPLE 39

2-[2-(cyclopentylamino)ethyl]-N-[1-[3-(trifluoromethyl)phenyl]ethyl]-4-(trifluoromethyl)-5-thiazolecarboxamide. $^1$H NMR (CDCl$_3$, 300 MHz): δ 7.61–7.43 (m, 4H), 6.42 (br d, J=7.0 Hz, 1H), 5.27 (app quint, J=7.1 Hz, 1H), 3.45 (t, J=5.7 Hz, 4H), 3.28 (s, 6H), 3.11 (t, J=6.4 Hz, 2H), 2.93 (t, J=6.4 Hz, 2H), 2.78 (t, J=5.7 Hz, 4H), 1.58 (d, J=7.0 Hz, 3H); LCMS (M+) 527, RT=1.430.

EXAMPLE 40

2-[2-(cyclopentylamino)ethyl]-N-[1-[3-(3-pyridinyl)phenyl]ethyl]-4-(trifluoromethyl)-5-thiazolecarboxamide. $^1$H NMR (CDCl$_3$, 300 MHz): δ 8.79–8.69 (m, 1H), 8.52 (d, J=4.4 Hz, 1H), 7.82 (d, J=7.7 Hz, 1H), 7.51 (s, 1H), 7.48–7.27 (m, 4H), 6.84 (br d, J=7.3 Hz, 1H), 5.29 (app quint, J=7.1 Hz, 1H), 3.42 (t, J=5.7 Hz, 4H), 3.25 (s, 6H), 3.08 (t, J=6.4 Hz, 2H), 2.90 (t, J=6.4 Hz, 2H), 2.75 (t, J=5.7 Hz, 4H), 1.61 (d, J=7.0 Hz, 3H); LCMS (M+) 536, RT=0.947.

EXAMPLE 41

2-[1-hydroxy-2-(1-piperidinyl)ethyl]-N-[1-[3-(trifluoromethoxy)phenyl]ethyl]-4-(trifluoromethyl)-5-thiazolecarboxamide. $^1$H NMR (CDCl$_3$, 300 MHz): δ 7.42–7.09 (m, 4H), 6.48 (br d, J=7.0 Hz, 1H), 5.22 (app quint, J=7.1 Hz, 1H), 4.97 (dd, J=4.4, 9.2 Hz, 1H), 4.48 (br s, 1H), 2.91 (dd, J=4.6, 12.6 Hz, 1H), 2.73–2.61 (m, 2H), 2.56 (ddd, J=2.3, 9.3, 12.0 Hz, 1H), 2.51–2.39 (m, 2H), 1.69–1.51 (m, 7H), 1.51–1.40 (m, 2H); LCMS (M+) 511, RT=1.440.

EXAMPLE 42

2-[1-hydroxy-2-(1-pyrrolidinyl)ethyl]-N-[1-[3-(trifluoromethyl)phenyl]ethyl]-4-(trifluoromethyl)-5-thiazolecarboxamide. $^1$H NMR (CDCl$_3$, 300 MHz): δ 7.60–7.42 (m, 4H), 6.60 (br d, J=7.0 Hz, 1H), 5.25 (app quint J=7.1 Hz, 1H), 4.99 (dd, J=4.4, 8.4 Hz, 1H), 4.51 (br s, 1H), 3.05 (dd, J=4.0, 12.4 Hz, 1H), 2.91 (ddd, J=2.2, 8.8, 12.4 Hz, 1H), 2.84–2.73 (m, 2H), 2.73–2.60 (m, 2H), 1.88–1.74 (m, 4H), 1.57 (d, J=7.0 Hz, 3H); LCMS (M+) 481, RT=1.373.

EXAMPLE 43

2-[1-hydroxy-[2-(2-furanylmethyl)methylamino]ethyl]-N-[1-[3-(trifluoromethyl)phenyl]ethyl]-4-(trifluoromethyl)-5-thiazolecarboxamide. $^1$H NMR (CDCl$_3$, 300 MHz): δ 7.60–7.42 (m, 4H), 7.39–7.33 (m, 1H), 6.46 (br d, J=7.0 Hz, 1H), 6.33–6.28 (m, 1H), 6.21 (d, J=3.3 Hz, 1H), 5.26 (app quint, J=7.1 Hz, 1H 4.91 (dd, J=4.4, 9.2 Hz, 1H), 3.68 (ABR q, J=14.6 Hz, Δν=23.7 Hz, 2H), 2.93 (ddd, J=1, 4.4, 12.8 Hz, 1H), 2.68 (ddd, J=2.6, 9.2, 12.8 Hz, 1H), 2.34 (s, 3H), 1.58 (d, J=7.0 Hz, 3H); LCMS (M+) 521, RT=1.447.

EXAMPLE 44

2-[hydroxy-[2-(cyclopropylmethyl)propylamino]ethyl]-N-[1-[3-trifluoromethoxy)phenyl]ethyl]-4-(trifluoromethyl)-5-thiazolecarboxamide. $^1$H NMR (CDCl$_3$, 300 MHz): δ 7.42–7.09 (m, 4H), 6.44 (br d, J=7.3 Hz, 1H), 5.23 (app quint, J=7.1 Hz, 1H), 4.91 (dd, J=4.4, 9.2 Hz, 1H), 3.10 (dd, J=4.4, 12.8 Hz, 1H), 2.80–2.51 (m, 3H), 2.47 (d, J=6.6 Hz, 2H), 1.61–1.41 (m, 5H), 0.94–0.81 (m, 4H), 0.62–0.46 (m, 2H), 0.20–0.06 (m, 2H); LCMS (M+) 539, RT=1.510.

The following examples were also made by the above methods.

| Example | Structure | Retention time (min) | MS (M+) |
|---|---|---|---|
| 45 | 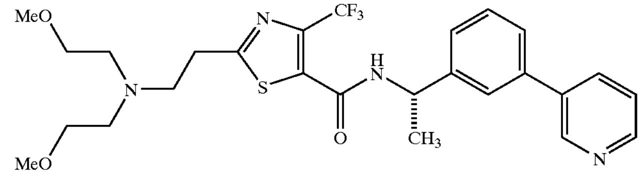 | 0.840 | 498 |
| 46 | 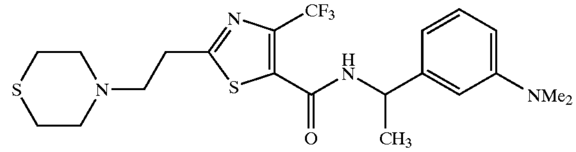 | 0.637 | 472 |

-continued

| Example | Structure | Retention time (min) | MS (M+) |
|---------|-----------|---------------------|---------|
| 47 | 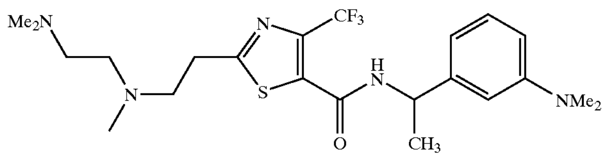 | 0.517 | 471 |
| 48 | 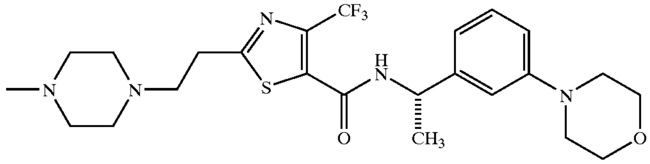 | 0.847 | 511 |
| 49 | 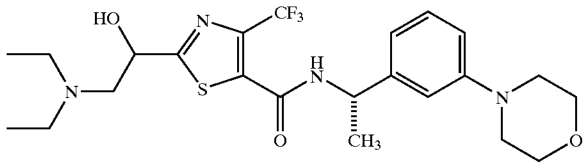 | 1.000 | 500 |
| 50 | 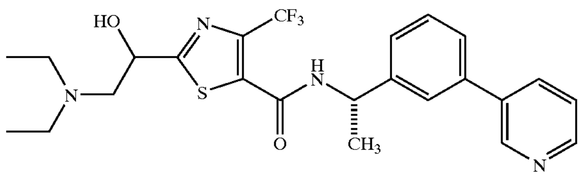 | 0.900 | 492 |
| 51 | 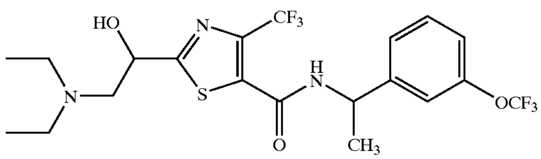 | 1.420 | 513 |
| 52 | 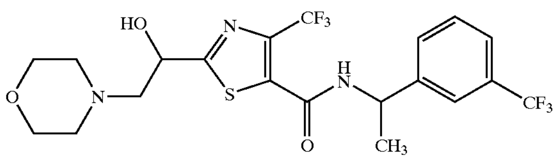 | 1.363 | 497 |
| 53 | 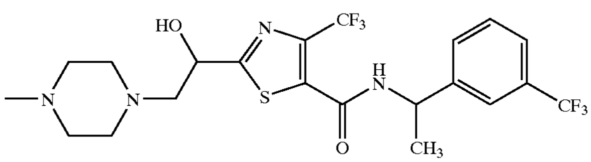 | 1.340 | 510 |
| 54 | 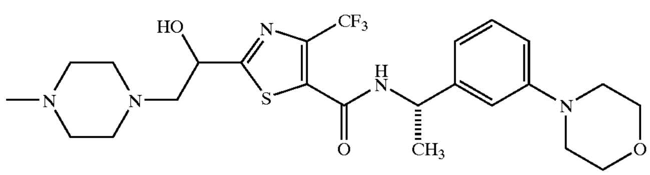 | 0.920 | 527 |

-continued
| Example | Structure | Retention time (min) | MS (M+) |
|---|---|---|---|
| 55 | 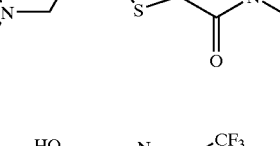 | 0.840 | 519 |
| 56 | 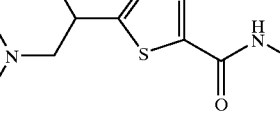 | 1.393 | 495 |
| 57 | 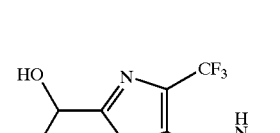 | 1.423 | 497 |
| 58 | 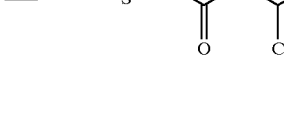 | 0.657 | 456 |
| 59 | 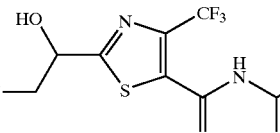 | 0.953 | 498 |
| 60 | 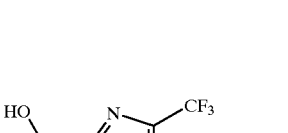 | 1.477 | 523 |
| 61 | 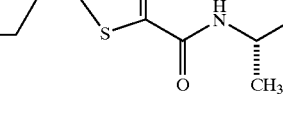 | 1.363 | 538 |

Method: 3 min run is 2 min gradient from 100% A to 100% B followed by 1 min at 100% B; solvent A: 10% MeOH/90% H$_2$O/0.1% TFA; solvent B: 90% MeOH/10% H$_2$O/0–1% TFA; Column: XTERRA 3.0×50 mm S7.

We claim:

1. A compound of Formula I or a pharmaceutically acceptable salt thereof

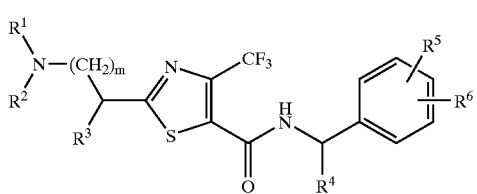

wherein
R$_1$ is C$_{1-6}$alkyl, C$_{3-7}$cycloalkyl, —(CH$_2$)$_{1-4}$C$_{3-7}$cycloalkyl, —(CH$_2$)$_{2-4}$N(C$_{1-6}$alkyl)$_2$, —(CH$_2$)$_{2-4}$OC$_{1-6}$alkyl,

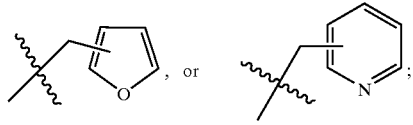

R$^2$ is hydrogen, C$_{1-6}$alkyl, or —(CH$_2$)$_{2-4}$OC$_{1-6}$alkyl;
or where R$^1$ and R$^2$ taken together are —CH$_2$CH$_2$XCH$_2$CH$_2$—, where X is a chemical bond, CH$_2$, CHOH, NH, NCH$_3$, NCOCH$_3$, O, or S;
R$^3$ is hydrogen or hydroxy, provided that where R$^3$ is hydroxy, m is not 0;
R$^4$ is hydrogen, C$_{1-6}$alkyl, hydroxymethyl, or trifluoromethyl;
R$^5$ is halogen, C$_{1-6}$alkyl, C$_{1-2}$perfluoroalkyl, C$_{1-6}$alkoxy, C$_{1-2}$perfluoroalkoxy, —N(R$^4$)$_2$, N-morpholinyl, or pyridyl;
R$^6$ is hydrogen, halogen, or C$_{1-6}$alkoxy;
m is 0 or 1.

2. A compound of claim 1 where R$^3$ is hydrogen and m is 1.

3. A compound of claim 2 where R$^4$ is methyl.

4. A compound of claim 3 selected from the following group:

2-[2-(4-morpholinyl)ethyl]-N-[1-[3-(3-pyridinyl)phenyl]ethyl]-4-(trifluoromethyl)-5-thiazolecarboxamide;
N-[1-[3-(dimethylamino)phenyl]ethyl]-2-[2-(1-pyrrolidinyl)ethyl]-4-(trifluoromethyl)-5-thiazolecarboxamide;
2-[2-(1-pyrrolidinyl)ethyl]-4-(trifluoromethyl)-N-[1-[3-(trifluoromethyl)phenyl]ethyl]-5-thiazolecarboxamide;
2-[2-[(2-furanylmethyl)methylamino]ethyl]-N-[(1S)-1-[3-(4-morpholinyl)phenyl]ethyl]-4-(trifluoromethyl)-5-thiazolecarboxamide;
2-[2-[(2-furanylmethyl)methylamino]ethyl]-N-[1-[3-(3-pyridinyl)phenyl]ethyl]-4-(trifluoromethyl)-5-thiazolecarboxamide;
2-[2-(1-pyrrolidinyl)ethyl]-N-[1-[3-(trifluoromethoxy)phenyl]ethyl]-4-(trifluoromethyl)-5-thiazolecarboxamide;
2-[2-[(2-furanylmethyl)methylamino]ethyl]-N-[1-[3-(trifluoromethoxy)phenyl]ethyl]-4-(trifluoromethyl)-5-thiazolecarboxamide;
2-[2-(diethylamino)ethyl]-N-[1-[3-(trifluoromethoxy)phenyl]ethyl]-4-(trifluoromethyl)-5-thiazolecarboxamide;
2-[2-(diethylamino)ethyl]-N-[1-[3-(dimethylamino)phenyl]ethyl]-4-(trifluoromethyl)-5-thiazolecarboxamide;
2-[2-[ethyl(4-pyridinylmethyl)amino]ethyl]-4-(trifluoromethyl)-N-[1-[3-(trifluoromethyl)phenyl]ethyl]-5-thiazolecarboxamide;
2-[2-(4-thiomorpholinyl)ethyl]-4-(trifluoromethyl)-N-[1-[3-(trifluoromethyl)phenyl]ethyl]-5-thiazolecarboxamide;
2-[2-[[2-(dimethylamino)ethyl]methylamino]ethyl]-N-[1-[3-(trifluoromethoxy)phenyl]ethyl]-4-(trifluoromethyl)-5-thiazolecarboxamide;
2-[2-[[2-(dimethylamino)ethyl]methylamino]ethyl]-4-(trifluoromethyl)-N-[1-[3-(trifluoromethyl)phenyl]ethyl]-5-thiazolecarboxamide;
2-[2-(4-methyl-1-piperazinyl)ethyl]-N-[1-[3-(trifluoromethoxy)phenyl]ethyl]-4-(trifluoromethyl)-5-thiazolecarboxamide;
2-[2-(1-piperidinyl)ethyl]-N-[1-[3-(trifluoromethoxy)phenyl]ethyl]-4-(trifluoromethyl)-5-thiazolecarboxamide;
N-[1-[3-(dimethylamino)phenyl]ethyl]-2-[2-(1-piperidinyl)ethyl]-4-(trifluoromethyl)-5-thiazolecarboxamide;
2-[2-(1-piperidinyl)ethyl]-4-(trifluoromethyl)-N-[1-[3-(trifluoromethyl)phenyl]ethyl]-5-thiazolecarboxamide;
N-[(1S)-1-[3-(4-morpholinyl)phenyl]ethyl]-2-[2-(1-piperidinyl)ethyl]-4-(trifluoromethyl)-5-thiazolecarboxamide;
2-[2-(4-hydroxy-1-piperidinyl)ethyl]-N-[1-[3-(trifluoromethoxy)phenyl]ethyl]-4-(trifluoromethyl)-5-thiazolecarboxamide;
2-[2-(4-hydroxy-1-piperidinyl)ethyl]-4-(trifluoromethyl)-N-[1-[3-(trifluoromethyl)phenyl]ethyl]-5-thiazolecarboxamide;
2-[2-[(cyclopropylmethyl)propylamino]ethyl]-N-[1-[3-(trifluoromethoxy)phenyl]ethyl]-4-(trifluoromethyl)-5-thiazolecarboxamide;
2-[2-[(cyclopropylmethyl)propylamino]ethyl]-N-[1-[3-(dimethylamino)phenyl]ethyl]-4-(trifluoromethyl)-5-thiazolecarboxamide;
2-[2-[(cyclopropylmethyl)propylamino]ethyl]-4-(trifluoromethyl)-N-[1-[3-(trifluoromethyl)phenyl]ethyl]-5-thiazolecarboxamide;
2-[2-(diethylamino)ethyl]-N-[(1S)-1-[3-(3-pyridinyl)phenyl]ethyl]-4-(trifluoromethyl)-5-thiazolecarboxamide;
2-[2-(1-piperidinyl)ethyl]-N-[(1S)-1-[3-(3-pyridinyl)phenyl]ethyl]-4-(trifluoromethyl)-5-thiazolecarboxamide;
2-[2-[(1-ethylpropyl)amino]ethyl]-N-[1-[3-(trifluoromethoxy)phenyl]ethyl]-4-(trifluoromethyl)-5-thiazolecarboxamide;
2-[2-[(1-ethylpropyl)amino]ethyl]-4-(trifluoromethyl)-N-[1-[3-(trifluoromethyl)phenyl]ethyl]-5-thiazolecarboxamide;
2-[2-[(2-furanylmethyl)amino]ethyl]-N-[(1S)-1-[3-(3-pyridinyl)phenyl]ethyl]-4-(trifluoromethyl)-5-thiazolecarboxamide;
2-[2-(cyclopentylamino)ethyl]-N-[1-[3-(trifluoromethoxy)phenyl]ethyl]-4-(trifluoromethyl)-5-thiazolecarboxamide;

2-[2-(cyclopentylamino)ethyl]-N-[(1S)-1-[3-(3-pyridinyl)phenyl]ethyl]-4-(trifluoromethyl)-5-thiazolecarboxamide;

2-[2-[bis(2-methoxyethyl)amino]ethyl]-N-[1-[3-(trifluoromethoxy)phenyl]ethyl]-4-(trifluoromethyl)-5-thiazolecarboxamide;

2-[2-[bis(2-methoxyethyl)amino]ethyl]-4-(trifluoromethyl)-N-[1-[3-(trifluoromethyl)phenyl]ethyl]-5-thiazolecarboxamide;

2-[2-[bis(2-methoxyethyl)amino]ethyl]-N-[(1S)-1-[3-(3-pyridinyl)phenyl]ethyl]-4-(trifluoromethyl)-5-thiazolecarboxamide;

2-[2-(4-morpholinyl)ethyl]-N-[(1S)-1-[3-(4-morpholinyl)phenyl]ethyl]-4-(trifluoromethyl)-5-thiazolecarboxamide;

N-[1-[3-(dimethylamino)phenyl]ethyl]-2-[2-(4-thiomorpholinyl)ethyl]-4-(trifluoromethyl)-5-thiazolecarboxamide;

2-[2-[[2-(dimethylamino)ethyl]methylamino]ethyl]-N-[1-[3-(dimethylamino)phenyl]ethyl]-4-(trifluoromethyl)-5-thiazolecarboxamide; and 2-[2-(4-methyl-1-piperazinyl)ethyl]-N-[(1S)-1-[3-(4-morpholinyl)phenyl]ethyl]-4-(trifluoromethyl)-5-thiazolecarboxamide.

5. A compound of claim 1 where $R^3$ is hydroxy and m is 1.

6. A compound of claim 5 where $R^4$ is methyl.

7. A compound of claim 6 selected from the following group:

2-[1-hydroxy-2-(1-piperidinyl)ethyl]-N-[1-[3-(trifluoromethoxy)phenyl]ethyl]-4-(trifluoromethyl)-5-thiazolecarboxamide;

2-[1-hydroxy-2-(1-pyrrolidinyl)ethyl]-4-(trifluoromethyl)-N-[1-[3-(trifluoromethyl)phenyl]ethyl]-5-thiazolecarboxamide;

2-[2-[(2-furanylmethyl)methylamino]-1-hydroxyethyl]-4-(trifluoromethyl)-N-[1-[3-(trifluoromethyl)phenyl]ethyl]-5-thiazolecarboxamide;

2-[2-[(cyclopropylmethyl)propylamino]-1-hydroxyethyl]-N-[1-[3-(trifluoromethoxy)phenyl]ethyl]-4-(trifluoromethyl)-5-thiazolecarboxamide;

2-[2-(diethylamino)-1-hydroxyethyl]-N-[(1S)-1-[3-(4-morpholinyl)phenyl]ethyl]-4-(trifluoromethyl)-5-thiazolecarboxamide;

2-[2-(diethylamino)-1-hydroxyethyl]-N-[(1S)-1-[3-(3-pyridinyl)phenyl]ethyl]-4-(trifluoromethyl)-5-thiazolecarboxamide;

2-[1-hydroxy-2-(4-morpholinyl)ethyl]-N-[1-[3-(trifluoromethoxy)phenyl]ethyl]-4-(trifluoromethyl)-5-thiazolecarboxamide;

2-[1-hydroxy-2-(4-morpholinyl)ethyl]-4-(trifluoromethyl)-N-[1-[3-(trifluoromethyl)phenyl]ethyl]-5-thiazolecarboxamide;

2-[1-hydroxy-2-(4-methyl-1-piperazinyl)ethyl]-4-(trifluoromethyl)-N-[1-[3-(trifluoromethyl)phenyl]ethyl]-5-thiazolecarboxamide;

2-[1-hydroxy-2-(4-methyl-1-piperazinyl)ethyl]-N-[(1S)-1-[3-(4-morpholinyl)phenyl]ethyl]-4-(trifluoromethyl)-5-thiazolecarboxamide;

2-[1-hydroxy-2-(4-methyl-1-piperazinyl)ethyl]-N-[(1S)-1-[3-(3-pyridinyl)phenyl]ethyl]-4-(trifluoromethyl)-5-thiazolecarboxamide;

2-[1-hydroxy-2-(1-piperidinyl)ethyl]-4-(trifluoromethyl)-N-[1-[3-(trifluoromethyl)phenyl]ethyl]-5-thiazolecarboxamide;

2-[1-hydroxy-2-(1-pyrrolidinyl)ethyl]-N-[1-[3-(trifluoromethoxy)phenyl]ethyl]-4-(trifluoromethyl)-5-thiazolecarboxamide;

N-[1-[3-(dimethylamino)phenyl]ethyl]-2-[1-hydroxy-2-(1-pyrrolidinyl)ethyl]-4-(trifluoromethyl)-5-thiazolecarboxamide;

2-[1-hydroxy-2-(1-pyrrolidinyl)ethyl]-N-[(1S)-1-[3-(4-morpholinyl)phenyl]ethyl]-4-(trifluoromethyl)-5-thiazolecarboxamide;

2-[2-[(cyclopropylmethyl)propylamino]-1-hydroxyethyl]-4-(trifluoromethyl)-N-[1-[3-(trifluoromethyl)phenyl]ethyl]-5-thiazolecarboxamide; and 2-[2-(4-acetyl-1-piperazinyl)-1-hydroxyethyl]-4-(trifluoromethyl)-N-[1-[3-(trifluoromethyl)phenyl]ethyl]-5-thiazolecarboxamide.

8. A compound of Formula Ie

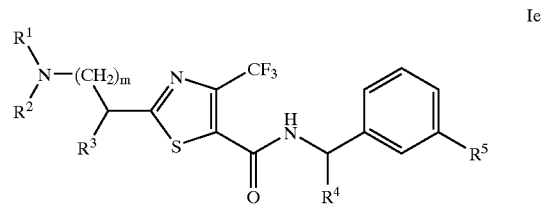

wherein $R^1$ is $C_{1-6}$alkyl, $C_{3-7}$cycloalkyl, —$(CH_2)_{1-4}C_{3-7}$cycloalkyl, —$(CH_2)_{2-4}N(C_{1-6}alkyl)_2$, —$(CH_2)_{2-4}OC_{1-6}$alkyl,

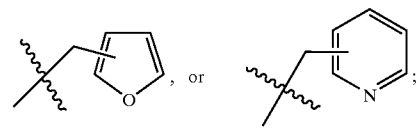

$R^2$ is hydrogen $C_{1-6}$alkyl, or —$(CH_2)_{2-4}OC_{1-6}$alkyl;
or where $R^1$ and $R^2$ taken together are —$CH_2CH_2XCH_2CH_2$—, where X is a chemical bond, $CH_2$, CHOH, NH, $NCH_3$, $NCOCH_3$, O, or S;

$R^3$ is hydrogen or hydroxy, provided that where $R^3$ is hydroxy, m is not 0;

$R^4$ is hydrogen, $C_{1-6}$alkyl, hydroxymethyl, or trifluoromethyl;

$R^5$ is halogen, $C_{1-6}$alkyl, $C_{1-2}$perfluoroalkyl, $C_{1-6}$alkoxy, $C_{1-2}$perfluoroalkoxy, —$N(R^4)_2$, N-morpholinyl, or pyridyl; and m is 0 or 1;

or a pharmaceutically acceptable salt thereof.

9. A compound of claim 1 where $R^1$, $R^2$, $R^3$, $R^4$, $R^5$, and $R^6$ are as defined in claim 1 and the structure has the stereochemical configuration of Formula Id.

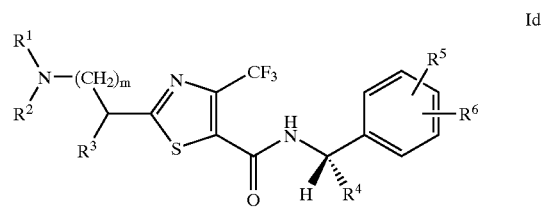

10. A pharmaceutical composition comprising a compound of Formula I claim 1 and a pharmaceutically acceptable carrier.

11. A method for the treatment of epilepsy which comprises administering to a mammal a therapeutically effective amount of the compound of claim 1.

* * * * *